(12) United States Patent
Dimino et al.

(10) Patent No.: US 9,320,913 B2
(45) Date of Patent: Apr. 26, 2016

(54) TWO-PART PULSED ELECTROMAGNETIC FIELD APPLICATOR FOR APPLICATION OF THERAPEUTIC ENERGY

(71) Applicant: Rio Grande Neurosciences, Inc., Sante Fe, NM (US)

(72) Inventors: Andre' A. Dimino, Woodcliff Lake, NJ (US); Matthew E. Drummer, Fort Lee, NJ (US)

(73) Assignee: Rio Grande Neurosciences, Inc., Santa Fe, NM (US)

( * ) Notice: Subject to any disclaimer, the term of this patent is extended or adjusted under 35 U.S.C. 154(b) by 0 days.

(21) Appl. No.: 14/688,602

(22) Filed: Apr. 16, 2015

(65) Prior Publication Data

US 2015/0297910 A1    Oct. 22, 2015

Related U.S. Application Data

(60) Provisional application No. 61/980,433, filed on Apr. 16, 2014, provisional application No. 62/086,987, filed on Dec. 3, 2014.

(51) Int. Cl.
*A61N 2/00* (2006.01)
*A61N 2/02* (2006.01)
*A61N 1/40* (2006.01)

(52) U.S. Cl.
CPC .... *A61N 2/02* (2013.01); *A61N 1/40* (2013.01)

(58) Field of Classification Search
CPC ........... A61N 1/40; A61N 2/00; A61N 2/002; A61N 2/004; A61N 2/006; A61N 2/008; A61N 2/02; A61N 2/06; A61N 2/12
See application file for complete search history.

(56) References Cited

U.S. PATENT DOCUMENTS

| 1,233,841 A | 7/1917 | Butcher |
| 2,130,758 A | 9/1938 | Rose |

(Continued)

FOREIGN PATENT DOCUMENTS

| CA | 0608693 | 11/1960 |
| CN | 1052053 A | 6/1991 |

(Continued)

OTHER PUBLICATIONS

Pilla et al.; U.S. Appl. No. 14/171,613 entitled "Apparatus and method for electromagnetic treatment of neurodegenerative conditions," filed Feb. 3, 2014.

(Continued)

*Primary Examiner* — Charles A Marmor, II
*Assistant Examiner* — Carrie R Dorna
(74) *Attorney, Agent, or Firm* — Shay Glenn LLP

(57) ABSTRACT

Pulsed electromagnetic field (PEMF) apparatuses and methods of making and using them. In particular, described herein are two-part PEMF apparatuses that include a self-contained, lightweight, small, compact (e.g., in some variations, wearable) generator unit that is adapted to releasably and replaceably mate with an applicator unit. The generator unit typically includes a power source and a controller that generated PEMF waveforms to be applied, including the shape and timing of the PEMF waveforms. The applicator unit typically includes a radio frequency (RF) power amplifier, a loop antenna, and impedance matching circuitry for matching the impedances for the connection between the antenna loop and the RF power amplifier. Thus, the generator module may control the application of PEMF signals without requiring impedance matching between the separable generator unit and the applicator unit. The applicator unit can include a plurality of variable capacitors that can be used to tune the PEMF signals.

17 Claims, 21 Drawing Sheets

(56) References Cited

U.S. PATENT DOCUMENTS

| | | |
|---|---|---|
| 2,276,996 A | 3/1942 | Milinowski |
| 2,648,727 A | 8/1953 | Rockwell |
| 3,043,310 A | 7/1962 | Milinowski |
| 3,181,535 A | 5/1965 | Milinowski |
| 3,270,746 A | 9/1966 | Kendall et al. |
| 3,329,148 A | 7/1967 | Kendall |
| 3,329,149 A | 7/1967 | Kendall at al. |
| 3,800,802 A | 4/1974 | Berry et al. |
| 3,890,953 A | 6/1975 | Kraus et al. |
| 3,915,151 A | 10/1975 | Kraus |
| 3,952,751 A | 4/1976 | Yarger |
| 3,978,864 A | 9/1976 | Smith |
| 4,028,518 A | 6/1977 | Boudouris et al. |
| 4,105,017 A | 8/1978 | Ryaby et al. |
| 4,197,851 A | 4/1980 | Fellus |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,340,063 A | 7/1982 | Maurer |
| 4,374,482 A | 2/1983 | Moore et al. |
| 4,428,366 A | 1/1984 | Findl et al. |
| 4,454,882 A | 6/1984 | Takano |
| 4,548,208 A | 10/1985 | Niemi |
| 4,550,714 A | 11/1985 | Talish et al. |
| 4,556,051 A | 12/1985 | Maurer |
| 4,616,629 A | 10/1986 | Moore |
| 4,627,438 A | 12/1986 | Liss et al. |
| 4,654,574 A | 3/1987 | Thaler |
| 4,672,951 A | 6/1987 | Welch |
| 4,674,482 A | 6/1987 | Waltonen et al. |
| 4,765,310 A | 8/1988 | Deagle |
| 4,793,325 A | 12/1988 | Cadossi et al. |
| 4,829,984 A | 5/1989 | Gordon |
| 4,850,372 A | 7/1989 | Ko et al. |
| 4,889,526 A | 12/1989 | Rauscher et al. |
| 4,926,881 A | 5/1990 | Ichinomiya et al. |
| 4,940,453 A | 7/1990 | Cadwell |
| 4,993,413 A | 2/1991 | McLeod et al. |
| 4,998,532 A | 3/1991 | Griffith |
| 5,000,178 A | 3/1991 | Griffith |
| 5,014,699 A | 5/1991 | Pollack et al. |
| 5,116,304 A | 5/1992 | Cadwell |
| 5,123,898 A | 6/1992 | Liboff et al. |
| 5,147,284 A | 9/1992 | Federov et al. |
| 5,181,902 A | 1/1993 | Erickson et al. |
| 5,224,922 A | 7/1993 | Kurtz |
| 5,314,401 A | 5/1994 | Tepper |
| 5,338,286 A | 8/1994 | Abbott et al. |
| 5,370,680 A | 12/1994 | Proctor |
| 5,386,837 A | 2/1995 | Sterzer |
| 5,407,421 A | 4/1995 | Goldsmith |
| 5,441,495 A | 8/1995 | Liboff et al. |
| 5,478,303 A | 12/1995 | Foley-Nolan et al. |
| 5,480,373 A | 1/1996 | Fischer et al. |
| 5,518,496 A | 5/1996 | McLeod et al. |
| 5,529,569 A | 6/1996 | Woo |
| 5,584,863 A | 12/1996 | Rauch et al. |
| 5,595,564 A | 1/1997 | Pinna |
| 5,707,334 A | 1/1998 | Young |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,778,894 A | 7/1998 | Dorogi et al. |
| 5,792,209 A | 8/1998 | Varner |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,968,527 A | 10/1999 | Litovitz |
| 5,990,177 A | 11/1999 | Brown |
| 5,997,464 A | 12/1999 | Blackwell |
| 6,004,257 A | 12/1999 | Jacobson |
| 6,083,149 A | 7/2000 | Wascher et al. |
| 6,086,525 A | 7/2000 | Davey et al. |
| 6,099,459 A | 8/2000 | Jacobson |
| 6,132,362 A | 10/2000 | Tepper et al. |
| 6,149,577 A | 11/2000 | Bouldin et al. |
| 6,155,966 A | 12/2000 | Parker |
| 6,190,893 B1 | 2/2001 | Shastri et al. |
| 6,200,259 B1 | 3/2001 | March |
| 6,213,934 B1 | 4/2001 | Bianco et al. |
| 6,231,187 B1 | 5/2001 | Munoz et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,301,506 B1 | 10/2001 | den Boer et al. |
| 6,321,120 B1 | 11/2001 | Surbeck et al. |
| 6,334,069 B1 | 12/2001 | George et al. |
| 6,348,070 B1 | 2/2002 | Teissl et al. |
| 6,418,345 B1 | 7/2002 | Tepper et al. |
| 6,421,562 B1 | 7/2002 | Ross |
| 6,424,863 B1 | 7/2002 | Flock et al. |
| 6,434,426 B1 | 8/2002 | Munneke et al. |
| 6,443,883 B1 | 9/2002 | Ostrow et al. |
| 6,450,941 B1 | 9/2002 | Larson |
| 6,458,151 B1 | 10/2002 | Saltiel |
| 6,458,157 B1 | 10/2002 | Suaning et al. |
| 6,463,336 B1 | 10/2002 | Mawhinney |
| 6,556,872 B2 | 4/2003 | Hauck |
| 6,560,489 B2 | 5/2003 | Hauck |
| 6,561,968 B1 | 5/2003 | Dissing et al. |
| 6,569,654 B2 | 5/2003 | Shastri et al. |
| 6,589,159 B2 | 7/2003 | Paturu |
| 6,629,971 B2 | 10/2003 | McDaniel |
| 6,648,812 B2 | 11/2003 | Ardizzone |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,839,589 B2 | 1/2005 | Petlan |
| 6,844,378 B1 | 1/2005 | Martin et al. |
| 6,919,205 B2 | 7/2005 | Brighton |
| 6,934,580 B1 | 8/2005 | Osorio et al. |
| 6,955,642 B1 | 10/2005 | Simon |
| 7,010,353 B2 | 3/2006 | Gan et al. |
| 7,022,506 B2 | 4/2006 | Brighton et al. |
| 7,089,060 B1 | 8/2006 | Fitzsimmons |
| 7,130,692 B2 | 10/2006 | Brighton et al. |
| 7,160,241 B1 | 1/2007 | Herbst |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,288,062 B2 | 10/2007 | Spiegel |
| 7,333,858 B2 | 2/2008 | Killian et al. |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,520,849 B1 | 4/2009 | Simon |
| 7,566,295 B2 | 7/2009 | Giardino et al. |
| 7,740,574 B2 | 6/2010 | Pilla et al. |
| 7,744,524 B2 | 6/2010 | Pilla |
| 7,758,490 B2 | 7/2010 | Pilla et al. |
| 7,896,797 B2 | 3/2011 | Pilla et al. |
| 8,167,784 B1 | 5/2012 | Honeycutt et al. |
| 8,343,027 B1 | 1/2013 | DiMino et al. |
| 8,415,123 B2 | 4/2013 | Pilla et al. |
| 8,961,385 B2 | 2/2015 | Pilla et al. |
| 2001/0007937 A1 | 7/2001 | MacKin |
| 2001/0031906 A1 | 10/2001 | Ishikawa et al. |
| 2001/0041820 A1 | 11/2001 | Woo |
| 2001/0044643 A1 | 11/2001 | Litovitz |
| 2002/0035358 A1 | 3/2002 | Wang |
| 2003/0023283 A1 | 1/2003 | McDaniel |
| 2003/0028072 A1 | 2/2003 | Fischell et al. |
| 2003/0093028 A1 | 5/2003 | Spiegel |
| 2003/0099979 A1 | 5/2003 | Ohtani et al. |
| 2003/0125769 A1 | 7/2003 | Brighton |

(56) References Cited

U.S. PATENT DOCUMENTS

| | | |
|---|---|---|
| 2003/0171640 A1 | 9/2003 | Canedo |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0267333 A1 | 12/2004 | Kronberg |
| 2005/0049640 A1 | 3/2005 | Gurtner et al. |
| 2005/0059153 A1 | 3/2005 | George et al. |
| 2005/0182287 A1 | 8/2005 | Becker |
| 2005/0215842 A1 | 9/2005 | Pilla et al. |
| 2005/0222625 A1 | 10/2005 | Laniado et al. |
| 2005/0251229 A1 | 11/2005 | Pilla et al. |
| 2006/0009825 A1 | 1/2006 | Chiriaev et al. |
| 2006/0161226 A1 | 7/2006 | McMickle |
| 2006/0206174 A1 | 9/2006 | Honeycutt et al. |
| 2006/0212077 A1 | 9/2006 | Pilla et al. |
| 2006/0293724 A1 | 12/2006 | Kronberg et al. |
| 2007/0026514 A1 | 2/2007 | Pilla et al. |
| 2007/0043254 A1 | 2/2007 | DeMarco |
| 2007/0060954 A1 | 3/2007 | Cameron et al. |
| 2007/0149901 A1 | 6/2007 | Gordon et al. |
| 2007/0173904 A1 | 7/2007 | Pilla |
| 2007/0203390 A1 | 8/2007 | Rohan et al. |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0039901 A1 | 2/2008 | Kronberg et al. |
| 2008/0058793 A1 | 3/2008 | Pilla et al. |
| 2008/0132971 A1 | 6/2008 | Pille et al. |
| 2008/0140155 A1 | 6/2008 | Pilla et al. |
| 2008/0200749 A1 | 8/2008 | Zheng et al. |
| 2008/0208287 A1 | 8/2008 | Palermo et al. |
| 2008/0217263 A1 | 9/2008 | Higgins et al. |
| 2008/0288035 A1 | 11/2008 | Gill et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0099623 A1 | 4/2009 | Bentwich |
| 2009/0105781 A1 | 4/2009 | Brighton |
| 2009/0216068 A1 | 8/2009 | Thomas et al. |
| 2009/0326315 A1 | 12/2009 | Nishi et al. |
| 2010/0004500 A1 | 1/2010 | Gliner et al. |
| 2010/0005571 A1 | 1/2010 | Moss et al. |
| 2010/0121407 A1 | 5/2010 | Pfaff et al. |
| 2010/0210893 A1 | 8/2010 | Pilla |
| 2010/0222631 A1 | 9/2010 | Pilla |
| 2011/0112352 A1 | 5/2011 | Pilla et al. |
| 2011/0152598 A1 | 6/2011 | Pilla et al. |
| 2011/0184223 A1 | 7/2011 | Peterchev et al. |
| 2011/0190849 A1 | 8/2011 | Faltys et al. |
| 2011/0213195 A1 | 9/2011 | Kraus et al. |
| 2012/0089201 A1 | 4/2012 | Pilla |
| 2012/0116149 A1 | 5/2012 | Pilla et al. |
| 2013/0035539 A1 | 2/2013 | Kornstein |
| 2013/0274540 A1 | 10/2013 | Pilla et al. |
| 2014/0046115 A1 | 2/2014 | Pilla |
| 2014/0046117 A1 | 2/2014 | Pilla |
| 2014/0213843 A1 | 7/2014 | Pilla et al. |
| 2014/0213844 A1 | 7/2014 | Pilla et al. |
| 2014/0303425 A1 | 10/2014 | Pilla et al. |

FOREIGN PATENT DOCUMENTS

| | | |
|---|---|---|
| CN | 1408448 A | 4/2003 |
| CN | 102006793 A | 4/2011 |
| CN | 102151362 A | 8/2011 |
| DE | 970276 | 9/1958 |
| EP | 543152 A2 | 10/1992 |
| EP | 0500983 | 7/1995 |
| EP | 1167070 A1 | 1/2002 |
| FR | 748828 | 4/1933 |
| GB | 0604107 | 6/1948 |
| GB | 2162066 | 1/1986 |
| GB | 2400316 A | 10/2004 |
| JP | 03-523271 | 8/2003 |
| WO | WO 83/01742 A1 | 5/1983 |
| WO | WO 95/27533 | 10/1995 |
| WO | WO 96/11723 | 4/1996 |
| WO | WO 2004/108208 A2 | 12/2004 |
| WO | WO 2005/051306 A2 | 6/2005 |
| WO | WO 2008/070001 A2 | 6/2008 |
| WO | WO 2009/155516 | 12/2009 |
| WO | WO 2010/067336 A2 | 6/2010 |
| WO | WO 2011/053607 A1 | 5/2011 |

OTHER PUBLICATIONS

Pilla et al.; U.S. Appl. No. 14/608,140 entitled "Devices and method for treatment of degenerative joint diseases with electromagnetic fields," filed Jan. 28, 2015.

Pilla; U.S. Appl. No. 14/687,716 entitled "Method and apparatus for electromagnetic enhancement of biochemical signaling pathways for therapeutics and prophylaxis in plants, animals and humans," filed 4/515/2015.

Aaron et al.; Power frequency fields promote cell differentiation coincident with an increase in transforming growth factor-?1 expression; Bioelectromagnetic; vol. 20 (7); pp. 453-458; Oct. 1999.

Aaron at al.; The conservative treatment of osteonecrosis of the femoral head. A comparison of core decompression and pulsing electromagnetic fields; Clin. Orthopaed. Rel. Res.; vol. 249; pp. 209-218; Dec. 1989.

Adair; A physical analysis of the ion parametric resonance model; Bioelectromagnetics; vol. 19(3); pp. 181-191; Dec. 1998.

Adair; Comment: Analyses of Models of Ion Actions Under the Combined Action of AC and DC Magnetic Fields; Bioelectromagnetics; vol. 27; No. 4; pp. 332-334; May 2006.

Adair; Criticism of Lednev's mechanism for the influence of weak magnetic fields on biological systems; Bioelectromagnetics; vol. 13 (3); pp. 231-235; Feb. 1992.

Adair; Static and low-frequency magnetic field effects: Health risks and therapies; Rep Prog Phys; vol. 63 (3); pp. 415-454; Mar. 2000.

Akai et al.; Effect of electrical stimulation on musculoskeletal systems: a meta-analysis of controlled clinical trials; Bioelectromagnetics; vol. 23 (2); pp. 132-143; Feb. 2002.

Albensi et al.; Diffusion and high resolution MRI of traumatic brain injury in rats: time course and correlation with histology. Exp Neurol 162, 61-72 (Mar. 2000).

Anderson et al.; Fluoro-jade B stains quiescent and reactive astrocytes in the rodent spinal cord. J Neurotrauma 20, 1223-31 (Nov. 2003).

Arendash et al.; Electromagnetic Field Treatment Protects Against and Reverses Cognitive Impairment in Alzheimer's Disease Mice. Journal of Alzheimer's Disease vol. 19, 191-210 (Jan. 2010).

Armonda et al.; Wartime traumatic cerebral vasospasm: recent review of combat casualties. Neurosurgery 59, 1215-25; discussion 1225 (Dec. 2006).

Arnold et al.; Nitric oxide activates guanylate cyclase and increases guanosine 3':5'-cyclic monophosphate levels in various tissue preparations. Proc Natl Acad Sci U S A 74, 3203-7 (Aug. 1977).

Auffray et al.; Blood monocytes: development, heterogeneity, and relationship with dendritic cells. Annu Rev Immunol 27, 669-92 (Jan. 2009).

Ayrapetyan et al.; Magnetic fields alter electrical properties of solutions and their physiological effects; Bioelectromagnetics; vol. 15 (2); pp. 133-142; (year of pub. sufficiently earlier than effective US filing date and any foreign priority date) 1994.

Barger et al.; Microglial Activation by Alzheimer Amyloid Precursor Protein and Modulation by Apolipoprotein E. Nature; vol. 388; 878-881 (Aug. 1997).

Bassett et al.; A non-operative salvage of surgically-resistant pseudoarthroses and non-unions by pulsing electromagnetic fields; Clin Orthop; vol. 124; pp. 117-131; May 1977.

Bassett et al.; Generation of electric potentials by bone in response to mechanical stress. Science 137, 1063-4 (Sep. 28, 1962).

Bassett, C. A.; Biological significance of piezoelectricity. Calc. Tiss. Res. 1, 252 (Dec. 1968).

Bawin et al.; Effects of modulated VHF fields on the central nervous system; Ann NY Acad Sci; vol. 247; pp. 74-81; Feb. 1975.

(56) References Cited

OTHER PUBLICATIONS

Bawin et al.; Sensitivity of calcium binding in cerebral tissue to weak environmental electric fields oscillating at low frequency; Proc Nat"l Acad Sci, USA; 73(6); pp. 1999-2003; Jun. 1976.

Bearden Jr.; Quantitation of submicrogram quantities of protein by an improved protein-dye binding assay; Biochim Biophys Acta; vol. 533(2); pp. 525-529; Apr. 26, 1978.

Beaumont et al.; The effects of human corticotrophin releasing factor on motor and cognitive deficits after impact acceleration injury. Neurol Res 22, 665-73 (Oct. 2000).

Beaumont et al.; The impact-acceleration model of head injury: injury severity predicts motor and cognitive performance after trauma. Neurol Res 21, 742-54 (Dec. 1999).

Beck et al.; The Bioelectromagnetics Society (History of the first 25 years); eds. Shappard, A. and Blackman, C.; 46 pgs.; (year of publication is sufficiently earlier than the effective U.S. filing date and any foreign priority date) 2004.

Becker, T. O.; The bioelectric factors in amphibian limb regeneration. J. Bone Joint Surg. 43A, 643 (Jul. 1961).

Bederson et al.; Nuclear magnetic resonance imaging and spectroscopy in experimental brain edema in a rat model. J Neurosurg 64, 795-802 (May 1986).

Belanger et al.; Cognitive sequelae of blast-related versus other mechanisms of brain trauma. J Int Neuropsychol Soc 15(1), 1-8 (Jan. 2009).

Belyaev et al.; Frequency-dependent Effects of ELF Magnetic Field on Cromatin Conformation in *Escherichia coli* Cells and Human Lymphocytes; Biochimica et Biophysica Acta; vol. 1526(3); pp. 269-276; Jun. 15, 2001.

Binder et al.; Pulsed electromagnetic field therapy of persistent rotator cuff tendinitis: a double blind controlled assessment; Lancet; vol. 1 (8379); pp. 695-697; Mar. 31, 1984.

Blackman et al.; A role for the magnetic field in the radiation induced efflux of calcium ions from brain tissue in vitro; Bioelectromagnetics; vol. 6(4); pp. 327-337; (year of pub. sufficiently earlier than effective US filing date and any foreign priority date) 1985.

Blackman et al.; Action of 50 Hz magnetic fields on neurite outgrowth in pheochromocytoma cells. Bioelectromagnetics 14, 273-86 (year of publication is sufficiently earlier than the effective U.S. filing date and any foreign priority date) (1993).

Blackman et al.; Effects of ELF fields on calcium-ion efflux from brain tissue in vitro; Radiat Res; vol. 92(3); pp. 510-520; Dec. 1982.

Blackman et al.; Empirical test of an ion parametric resonance model for magnetic field interactions with PC-12 cells; Bioelectromagnetics; vol. 15(3): pp. 239-260; (year of pub. sufficiently earlier than effective US filing date and any foreign priority date) 1994.

Blackman et al.; Influence of electromagnetic fields on the efflux of calcium ions from brain tissue in vitro: A three-model analysis consistent with the frequency response up to 510 Hz; Bioelectromagnetics; vol. 9(3); pp. 215-227; (year of pub. sufficiently earlier than effective US filing date and any foreign priority date) 1988.

Blackman et al.; Multiple power-density windows and their possible origin; Bioelectromagnetics; vol. 10(2); pp. 115-128; (year of pub. sufficiently earlier than effective US filing date and any foreign priority date) 1989.

Blanchard et al.; Clarification and application of an ion parametric resonance model for magnetic field interactions with biological systems; Bioelectromagnetics; vol. 15(3); pp. 217-238; (year of pub. sufficiently earlier than effective US filing date and any foreign priority date) 1994.

Blank et al.; Do electromagnetic fields interact directly with DNA?; Bioelectromagnetics; vol. 18(2); pp. 111-115; (year of pub. sufficiently earlier than effective US filing date and any foreign priority date) 1997.

Blumenthal et al.; Effects of low-intensity AC and/or DC electromagnetic fields on cell attachment and induction of apoptosis; Bioelectromagnetics; vol. 18(3); pp. 264-272; (year of pub. sufficiently earlier than effective US filing date and any foreign priority date) 1997.

Borbely et al.; Pulsed high-frequency electromagnetic field affects human sleep electroencephalogram. Neurosci Lett 275, 207-10 (Nov. 19, 1999).

Bracken et al.; Administration of methylprednisolone for 24 or 48 hours or tirilazad mesylate for 48 hours in the treatment of acute spinal cord injury. Results of the Third National Acute Spinal Cord Injury Randomized Controlled Trial. National Acute Spinal Cord Injury Study. Jama 277, 1597-604 (May 28, 1997).

Bredt, D. S.; Nitric oxide signaling specificity—the heart of the problem. J Cell Sci 116, 9-15 (Jan. 2003).

Brighton et al.; Signal transduction in electrically stimulated bone cells. J Bone Joint Surg Am 83-A, 1514-23 (Oct. 2001).

Brighton, C. T.; The treatment of non-unions with electricity. J Bone Joint Surg Am 63, 847-51 (Jun. 1981).

Brooks et al.; Magnetic resonance spectroscopy in traumatic brain injury. J Head Trauma Rehabil 16, 149-64 (Apr. 2001).

Burton, T.; New Test for Brain Injury on Horizon, The Wall Street Journal, New York, (Jul. 20, 2010).

Cain; Stimulating Treatment; Orthopedic Technology Review; vol. 4; No. 4; pp. 31-34; Jul.-Aug. 2002.

Cammermeyer, J.; I. An evaluation of the significance of the "dark" neuron. Ergeb Anat Entwicklungsgesch 36, 1-61 (year of publication is sufficiently earlier than the effective U.S. filing date and any foreign priority date) (1962).

Canals et al.; Neurotrophic and neurotoxic effects of nitric oxide on fetal midbrain cultures. J Neurochem 76, 56-68 (Jan. 2001).

Canseven et al.; Effects of ambient ELF magnetic fields: variations in electrolyte levels in the brain and blood plasma; Gazi Tip Dergisi / Gazi Medical Journal; 16(3); pp. 121-127; Sep. 2005.

Casper et al.; Dopaminergic neurons associate with blood vessels in neural transplants. Exp Neurol 184, 785-93 (Dec. 2003).

Casper et al.; Enhanced vascularization and survival of neural transplants with ex vivo angiogenic gene transfer. Cell Transpl. 11, 331-349 (year of publication is sufficiently earlier than the effective U.S. filing date and any foreign priority date) (2002).

Cederberg et al.; What has inflammation to do with traumatic brain injury? Childs Nerv Syst 26, 221-6 (Feb. 2010).

Cernak et al.; Cognitive deficits following blast injury-induced neurotrauma: possible involvement of nitric oxide. Brain Inj 15, 593-612 (Jul. 2001).

Cernak et al.; Traumatic brain injury: an overview of pathobiology with emphasis on military populations. J Cereb Blood Flow Metab 30, 255-66 (Feb. 2010).

Cernak et al.; Ultrastructural and functional characteristics of blast injury-induced neurotrauma. J Trauma 50, 695-706 (Apr. 2001).

Chiabrera et al.; Bioelectromagnetic Resonance Interactions: Endogenous Field and Noise. In "Interaction Mechanisms of Low-Level Electromagnetic Fields in Living Systems." Oxford University Press. 164.179; Dec. 1992.

Chiabrera et al.; Effect of Lifetimes on Ligand Binding Modelled by the Density Operator; Bioelectrochemistry and Bioenergetics; vol. 30; pp. 35-42; Mar. 1993.

Chiabrera et al.; Quantum dynamics of ions in molecular crevices under electromagnetic exposure; (Brighton C, Pollak S, editors); Electromagnetics in biology and medicine; San Francisco, USA; San Francisco Press; pp. 21-26; Jun. 1991.

Chiabrera et al.; The role of the magnetic field in the EM interaction with ligand binding; In: "Mechanistic Approaches to Interaction of Electric and Electromagnetic Fields With Living Systems;" Blank, Findl(eds); New York; Plenum Press; pp. 79-95; Oct. 31, 1987.

Ciani et al.; Akt pathway mediates a cGMP-dependent survival role of nitric oxide in cerebellar granule neurones. J Neurochem 81, 218-28 (Apr. 2002).

Clapham, D.; Calcium signaling; Cell; vol. 80; pp. 259-268; Jan. 27, 1995.

Clausen et al.; Neutralization of interleukin-1? modifies the inflammatory response and improves histological and cognitive outome following traumatic brain injury in mice. European Journal of Neuroscience; vol. 30; pp. 385-396; Aug. 30, 2009.

Colbert et al.; Magnetic mattress pad use in patients with fibromyalgia: A randomized double-blind pilot study; J Back Musculoskeletal Rehab; vol. 13(1); 19-31; Jan. 1999.

(56) References Cited

OTHER PUBLICATIONS

Collacott et al.; Bipolar permanent magnets for the treatment of low back pain: A pilot study; JAMA; vol. 283; No. 10; pp. 1322-1325; Mar. 8, 2000.
Colomer et al.; Physiological roles of the Ca2+/CaM-dependent protein kinase cascade in health and disease. Subcell Biochem 45, 169-214 (year of publication is sufficiently earlier than the effective U.S. filing date and any foreign priority date) (2007).
Cook et al.; Resting EEG is affected by exposure to a pulsed ELF magnetic field. Bioelectromagnetics 25, 196-203 (Apr. 2004).
Cook et al.; The effects of pulsed, high-frequency radio waves on the rate of osteogenesis in the healing of extraction wounds in dogs; Oral Sug.; 32(6); (Dec. 1971).
Cork et al.; Computer-aided analysis of polarized neurite growth. Effects of applied electrical fields on neuronal development. J Neurosci Methods 32, 45-54 (Apr. 1990).
Courtney et al.; A thoracic mechanism of mild traumatic brain injury due to blast pressure waves. Med Hypotheses 72, 76-83 (Jan. 2009).
Cox, J.; Interactive Properties of Calmodulin; Biochem J.; vol. 249(3); pp. 621-629; Feb. 1, 1988.
Csuka et al.; IL-10 levels in cerebrospinal fluid and serum of patients with severe traumatic brain injury: relationship to IL-6, TNF-alpha, TGF-beta1 and blood-brain barrier function. J Neuroimmunol 101, 211-21 (Nov. 1999).
Czosnyka, et al.; Montoring and Interpretation of Intracranial Pressure. J. Neurol Neurosurg Psychiatry; vol. 75, 813-821; (Jun. 2004).
De Olmos et al.; Use of an amino-cupric-silver technique for the detection of early and semiacute neuronal degeneration caused by neurotoxicants, hypoxia, and physical trauma. Neurotoxicol Teratol 16, 545-61 (Nov. 1994).
Dixon et al.; A controlled cortical impact model of traumatic brain injury in the rat. J Neurosci Methods 39, 253-62 (Oct. 1991).
Dixon et al.; A fluid percussion model of experimental brain injury in the rat. J Neurosurg 67, 110-9 (Jul. 1987).
Edmonds, D.; Larmor precession as a mechanism for the detection of static and alternating magnetic fields; Bioelectrochemistry and Bioenergetics; vol. 30; pp. 3-12; Mar. 1993.
Edwards et al.; Final results of MRC CRASH, a randomised placebo controlled trial of intravenous corticosteroid in adults with head injury-outcomes at 6 months. Lancet 365, 1957-9 (Jun. 2005).
Elder et al.; Blast-related mild traumatic brain injury: mechanisms of injury and impact on clinical care. Mt Sinai J Med 76, 111-8 (Apr. 2009).
Elder et al.; Increased locomotor activity in mice lacking the low-density lipoprotein receptor. Behav Brain Res 191, 256-65 (Aug. 2008).
Engström, S.; Dynamic properties of Lednev's parametric resonance mechanism; Bioelectromagnetics; vol. 17(1); pp. 58-70; (year of pub. sufficiently earlier than effective US filing date and any foreign priority date) 1996.
Fabre et al.; Antidepressant efficacy and cognitive effects of repetitive transcranial magnetic stimulation in vascular depression: an open trial. Int J Geriatr Psychiatry 19, 833-42 (Sep. 2004).
Farndale et al.; The action of pulsed magnetic fields on cyclic AMP levels in cultured fibroblasts. Biochim Biophys Acta 881, 46-53 (Mar. 19, 1986).
Farrarelli et al.; Breakdown in cortical effective connectivity during midazolam-induced loss of consciousness. Proc Natl Acad Sci U S A 107, 2681-6 (Feb. 9, 2010).
Fassbender et al.; Temporal profile of release of interleukin-1beta in neurotrauma. Neurosci Lett 284, 135-8 (Apr. 2000).
Faul et al.; Traumatic brain injury in the United States (Emergency department visits, hospitalization and deaths 2002-2006); U.S. Dept. of Health and Human Services, 74 pgs.; Mar. 2010.
Fetler et al.; Brain under surveillance: the microglia patrol. Science 309, 392-3 (Jul. 15, 2005).
Fitzsimmons et al.; A pulsing electric field (PEF) increases human chondrocyte proliferation through a transduction pathway involving nitric oxide signaling. J Orthop Res 26, 854-9 (Jun. 2008).
Fitzsimmons et al.; Combined magnetic fields increase net calcium flux in bone cells. Calcif. Tiss. Intl.; vol. 55; pp. 376-380; Nov. 1994.
Foda et al.; A new model of diffuse brain injury in rats. Part II: Morphological characterization. J Neurosurg 80, 301-13 (Feb. 1994).
Foley-Nolan et al.; Pulsed high frequency (27MHz) electromagnetic therapy for persistent neck pain. A double blind, placebo-controlled study of 20 patients. Orthopedics 13, 445-51 (Apr. 1990).
Friedman et al.; Quantitative proton MRS predicts outcome after traumatic brain injury. Neurology 52, 1384-91 (Apr. 1999).
Fukada et al.; On the piezoelectric effect of bone. J Phys Soc Japan 12(10), 1158-1162 (Oct. 1957).
Gaetz, M.; The neurophysiology of brain injury. Clin Neurophysiol 115, 4-18 (Jan. 2004).
Garthwaite et al.; Cyclic GMP and cell death in rat cerebellar slices. Neuroscience 26, 321-6 (Jul. 1988).
Gasparovic et al.; Decrease and recovery of N-acetylaspartate/creatine in rat brain remote from focal injury. J Neurotrauma 18, 241-6 (Mar. 2001).
Ghirnikar et al.; Inflammation in traumatic brain injury: role of cytokines and chemokines. Neurochem Res 23, 329-40 (Mar. 1998).
Ginsberg, A. J.; Ultrashort radio waves as a therapeutic agent. Med Record 140, 651-653 (Dec. 19, 1934).
Glass et al.*; Mechanisms underlying inflammation in neurodegeneration. Cell 140, 918-34 (Mar. 19, 2010).
Goligorsky et al.; Relationships between caveolae and eNOS: everything in proximity and the proximity of everything; Am J Physiol Renal Physiol; 283; pp. F1-F10; Jul. 2002.
Gona et al.; Effects of 60 Hz electric and magnetic fields on the development of the rat cerebellum. Bioelectromagnetics 14, 433-47 (year of publication is sufficiently earlier than the effective U.S. filing date and any foreign priority date) (1993).
Goodwin et al.; A double-blind study of capacitively coupled electrical stimulation as an adjunct to lumbar spinal fusions(printed from online source). Spine 24(13), 1349-1357 (Jul. 1999).
Graeber et al.; New expression of myelomonocytic antigens by microglia and perivascular cells following lethal motor neuron injury. J Neuroimmunol 27, 121-32 (May 1990).
Greenebaum et al.; Effects of pulsed magnetic fields on neurite outgrowth from chick embryo dorsal root ganglia. Bioelectromagnetics 17, 293-302 (year of publication is sufficiently earlier than the effective U.S. filing date and any foreign priority date) (1996).
Halle, B.; On the cyclotron resonance mechanism for magnetic field effects on transmembrane ion conductivity; Bioelectromagnetics; vol. 9(4); pp. 381-385; (year of pub. sufficiently earlier than effective US filing date and any foreign priority date) 1988.
Hart, F.; A quantum mechanical model for bioelectromagnetic resonance phenomena; J Bioelectr; vol. 9; pp. 1-7; Jan. 1990.
Hellmich et al.; Dose-dependent neuronal injury after traumatic brain injury; Brain Research; 1044; pp. 144-154 (May 2005).
Hutchinson et al.; Inflammation in human brain injury: intracerebral concentrations of IL-1alpha, IL-1beta, and their endogenous inhibitor IL-1ra. J Neurotrauma 24, 1545-57 (Oct. 2007).
Ignarro et al.; Heme-dependent activation of guanylate cyclase by nitric oxide: a novel signal transduction mechanism. Blood Vessels 28, 67-73 (Nov.-Dec. 1991).
Ito et al.; Characterization of edema by diffusion-weighted imaging in experimental traumatic brain injury. J Neurosurg 84, 97-103 (Jan. 1996).
Itoh et al.; Accelerated wound healing of pressure ulcers by pulsed high peak power electromagnetic energy (Diapulse). Decubitus 4(1), pp. 24-25, 29-30, 32 & 34 (Feb. 1991).
Jackson et al.; The demonstration of new human brain-specific proteins by high-resolution two-dimensional polyacrylamide gel electrophoresis. J Neurol Sci 49, 429-38; (Mar. 1981).
Jenrow et al.; Weak ELF magnetic field effects on hippocampal rhythmic slow activity. Exp Neurol 153, 328-34 (Oct. 1998).
Johansson, et al.; Brij 58, a polyoxethylene acyl ether, creates membrane vesicles of uniform sidedness: A new tool to obtain inside-out (cytoplasmic side-out) plasma membrane vesicle; Plant J.; vol. 7(1); pp. 165-173; Jan. 1995.
Jokela et al.; Assessment of the magnetic field exposure due to the battery current of digital mobile phones. Health Phys 86, 56-66 (Jan. 2004).

(56) References Cited

OTHER PUBLICATIONS

Jones et al.; Low energy time varying electromagnetic field interactions with cellular control mechanisms; In: fMechanistic approaches to interactions of electric and electromagnetic fields with living systemsf; Blank, Findl (eds); Plenum Press; NY; pp. 389-397; Oct. 31, 1987.
Jortner, B. S.; The return of the dark neuron. A histological artifact complicating contemporary neurotoxicologic evaluation. Neurotoxicology 27, 628-34 (Jul. 2006).
Kamm et al.; The effect of traumatic brain injury upon the concentration and expression of interleukin-1beta and interleukin-10 in the rat. J Trauma 60, 152-7 (Jan. 2006).
Kanje et al.; Pretreatment of rats with pulsed electromagnetic fields enhances regeneration of the sciatic nerve. Bioelectromagnetics 14, 353-9 (year of publication is sufficiently earlier than the effective U.S. filing date and any foreign priority date) (1993).
Kimura et al.; Reciprical regulation between nitric oxide and vascular endothelial growth factor in angiogenesis; Acta Biochimica Polonica; vol. 50, No. 1; pp. 49-59; (year of publication is sufficiently earlier than the effective U.S. filing date and any foreign priority date) 2003.
Kingham et al.; Microglial secreted cathepsin B induces neuronal apoptosis. J Neurochem 76, 1475-84 (Mar. 2001).
Kjellbom et al.; Preparation and polypeptide composition of chlorophyll-free plasma membranes from leaves of light-grown spinach and barley; Physiol Plant; vol. 62; pp. 501-509; Dec. 1984.
Kloth et al.; Effect of Pulsed Radio Frequency Stimulation on Wound Healing: A Double-Blind Pilot Clinical Study; in "Electricity and Magnetism in Biology and Medicine"; Bersani F, ed Plenum, New York; pp. 875-878; (year of pub. sufficiently earlier than effective US filing date and any foreign priority date) 1999.
Knowles et al.; Nitric oxide synthases in mammals. Biochem J 298, 249-58 (Mar. 1994).
Koch, et al.; Interaction between weak low-frequency magnetic fields and cell membranes; Bioelectromagnetics; vol. 24(6); pp. 39-402; Sep. 2003.
Körner et al.; Surface properties of right side-out plasma membrane vesicles isolated from barley roots and leaves; Plant Physiol.; vol. 79(1); pp. 72-79; Sep. 1985.
Kossmann et al.; Intrathecal and serum interleukin-6 and the acute-phase response in patients with severe traumatic brain injuries. Shock 4, 311-7 (Nov. 1995).
Kramarenko et al.; Effects of high-frequency electromagnetic fields on human EEG: a brain mapping study. Int J Neurosci 113, 1007-19 (Jul. 2003).
Lai et al.; Magnetic-field-induced DNA strand breaks in brain cells of the rat. Environ Health Perspect 112, 687-94 (May 2004).
Langlois et al.; The epidemiology and impact of traumatic brain injury: a brief overview. J Head Trauma Rehabil 21, 375-8 (Aug. 2006).
Lansdown et al.; Sequential changes in trace metal, metallothionein and calmodulin concentrations in healing skin wounds; J. Anat.; vol. 195(Pt 3); pp. 375-386; Oct. 1999.
Larsson et al.; Isolation of highly purified plant plasma membranes and separation of inside-out and rightside-out vesicles; Methods Enzymol; vol. 228; pp. 451-469; (year of pub. sufficiently earlier than effective US filing date and any foreign priority date) 1994.
Lednev, V.; Possible mechanism for the effect of weak magnetic fields on biological systems: Correction of the basic expression and its consequences; In: Electricity and magnetism in biology and medicine Blank (eds.); San Francisco, CA; San Francisco Press, Inc.; pp. 550-552; Oct. 1993.
Lednev, V.; Possible mechanism for the influence of weak magnetic fields on biological systems; Bioelectromagnetics; vol. 12; pp. 71-75; (year of publication is sufficiently earlier than the effective U.S. filing date and any foreign priority date) 1991.
LeDoux, J.; Emotion: clues from the brain. Annu Rev Psychol 46, 209-35 (Jan. 1995).
Lee et al.; Nitric oxide in the healing wound: a time-course study. J Surg Res 101, 104-8 (Nov. 2001).
Lee et al.; Pulsed magnetic and electromagnetic fields in experimental achilles tendonitis in the rat: a prospective randomized study. Arch Phys Med Rehabil 78, 399-404 (Apr. 1997).
Lescot et al.; Temporal and regional changes after focal traumatic brain injury. J Neurotrauma 27, 85-94 (Jan. 2010).
Liboff, et al.; Experimental evidence for ion cyclotron resonance mediation of membrane transport; In: Blank, Findl (eds.); Mechanical approaches to interactions of electric and electromagnetic fields with living systems; Blank, Findl (eds.); New York; Plenum Press; pp. 281-296; Oct. 31, 1987.
Liboff, et al.; Geomagnetic cyclotron resonance in living cells; J Biol Phys; vol. 13(4); pp. 99-102; Dec. 1985.
Liboff, et al.; Kinetics of channelized membrane ions in magnetic fields; Bioelectromagnetics; vol. 9(1); pp. 39-51; (year of pub. sufficiently earlier than effective US filing date and any foreign priority date) 1988.
Lighthall, J. W.; Controlled cortical impact: a new experimental brain injury model. J Neurotrauma 5, 1-15 (year of publication is sufficiently earlier than the effective U.S. filing date and any foreign priority date) (1988).
Likic et al.; Dynamics of Ca2+-saturated Calmodulin D129N Mutant Studied by Multiple Molecular Dynamics Simulations; Protein Sci; vol. 12(10); pp. 2215-2229; Oct. 2003.
Lincoln et al.; Low frequency of pathogenic mutations in the ubiquitin carboxy-terminal hydrolase gene in familial Parkinson's disease. Neuroreport 10, 427-9 (Feb. 1999).
Ling et al.; Explosive blast neurotrauma. J Neurotrauma 26, 815-25 (Jun. 2009).
Linovitz et al.; Combined magnetic fields accelerate and increase spine fusion: a double-blind, randomized, placebo controlled study(printed from online source). Spine 27, 1383-1389 (Jul. 2002).
Liu et al.; Ubiquitin C-terminal hydrolase-L1 as a biomarker for ischemic and traumatic brain injury in rats (Author Manuscript). Eur J Neurosci 31(4), 722-32 (Feb. 2010).
Louin et al.; Selective inhibition of inducible nitric oxide synthase reduces neurological deficit but not cerebral edema following traumatic brain injury. Neuropharmacology 50, 182-90 (Feb. 2006).
Lukas, T.; A Signal Transduction Pathway Model Prototype II: Application to Ca2+-Calmodulin Signaling and Myosin Light Chain Phosphorylatiori; Biophysical Journal; vol. 87(3); pp. 1417-1425; Sep. 2004.
Maas et al.; Moderate and severe traumatic brain injury in adults. Lancet Neurol 7, 728-41 (Aug. 2008).
Maas et al.; Prognosis and clinical trial design in traumatic brain injury: the IMPACT study. J Neurotrauma 24, 232-8 (Feb. 2007).
Maas et al.; Why have recent trials of neuroprotective agents in head injury failed to how convincing efficacy? A pragmatic analysis and theoretical considerations. (printed from online source) Neurosurgery 44, 1286-98 (Jun. 1999).
Madhusoodanan et al.; NO-cGMP signaling and regenerative medicine involving stem cells. Neurochem Res 32, 681-94 (Apr.-May 2007).
Maeda et al.; Effect of water on piezoelectric, dielectric, and elastic properties of bone; Biopolymers 21(10); 2055-2068 (Oct. 1982).
Man, et al.; The influence of permanent magnetic field therapy on wound healing in suction lipectomy patients: A double-blind study; Plastic and Reconstructive Surgery; vol. 104(7); pp. 2261-2296; Dec. 1999 (printed Jul. 17, 2010).
Markov, et al.; Weak static magnetic field modulation of myosin phosphorylation in a cell-free preparation: Calcium dependence; Bioelectrochemistry and Bioenergetics; vol. 43(2); pp. 233-238; Aug. 1997.
Marmarou et al.; A new model of diffuse brain injury in rats. Part I: Pathophysiology and biomechanics. J Neurosurg 80, 291-300 (Feb. 1994).
Martin et al.; Parkinson's disease alpha-synuclein transgenic mice develop neuronal mitochondrial degeneration and cell death. J Neurosci 26, 41-50 (Jan. 2006).
McDonald, F.; Effect of static magnetic fields on osteoblasts and fibroblasts in-vitro; Bioelectomagnetics; vol. 14(3); pp. 187-196; (year of pub. sufficiently earlier than effective US filing date and any foreign priority date) 1993.

(56) References Cited

OTHER PUBLICATIONS

McFarlane et al.; Changes in neurite outgrowth but not in cell division induced by low EMF exposure: influence of field strength and culture conditions on responses in rat PC12 pheochromocytoma cells. Bioelectrochemistry 52, 23-8 (Sep. 2000).
McIntosh et al.; Traumatic brain injury in the rat: characterization of a lateral fluid-percussion model. Neuroscience 28(1), 233-44 (year of publication is sufficiently earlier than the effective U.S. filing date and any foreign priority date) (1989).
McIntosh et al.; Traumatic brain injury in the rat: characterization of a midline fluid-percussion model. Cent Nerv Syst Trauma 4, 119-34 (year of publication is sufficiently earlier than the effective U.S. filing date and any foreign priority date) (1987).
McLean, et al.; Blockade of sensory neuron action potentials by a static magnetic field in the 10 mT range; Bioelectromagnetics; vol. 16(1); pp. 20-32; (year of pub. sufficiently earlier than effective US filing date and any foreign priority date) 1995.
McLeod, et al.; Dynamic characteristics of membrane ions in multifield configurations of low-frequency electromagnetic radiation; Bioelectromagnetics; vol. 7(2); pp. 177-189; (year of pub. sufficiently earlier than effective US filing date and any foreign priority date) 1986.
Mehler, et al.; Structural Dynamics of Calmodulin and Troponin C; Protein Engineering; vol. 4; No. 6; pp. 625-627; Aug. 1991.
Mellor, S.; The pathogenesis of blast injury and its management. Br J Hosp Med 39, 536-9 (Jun. 1988).
Mont et al.; Pulsed electrcial stimulation to defer TKA in patients with knee osteoarthritis; The Cutting Edge; 29(10); pp. 887-892 (Oct. 2006).
Mooney; A randomized double blind prospective study of the efficacy of pulsed electromagnetic fields for interbody lumbar fusions; Spine; vol. 15(7); pp. 708-715; Jul. 1990.
Morganti-Kossmann et al.; Production of cytokines following brain injury: beneficial and deleterious for the damaged tissue. Mol Psychiatry 2, 133-6 (Mar. 1997).
Morris et al.; Place navigation impaired in rats with hippocampal lesions. Nature 297, 681-3 (Jun. 1982).
Muehsam et al.; Lorentz Approach to Static Magnetic Field Effects on Bound Ion Dynamics and Binding Kinetics: Thermal Noise Considerations; Bioelectromagnetics; vol. 17(2); pp. 89-99; (year of pub. sufficiently earlier than effective US filing date and any foreign priority date) 1996.
Muehsam et al.; Weak Magnetic Field Modulation of Ion Dynamics in a Potential Well: Mechanistic and Thermal Noise Considerations; Bioelectrochem. & Bioenergetics; vol. 35; pp. 71-79; Nov. 1994.
Muehsam, et al.; The sensitivity of cells and tissues to exogenous fields: effects of target system initial state; Bioelectrochemistry and Bioenergetics; vol. 48(1); pp. 35-42; Feb. 1999.
Naldini et al.; Role of inflammatory mediators in angiogenesis. Curr Drug Targets Inflamm Allergy 4, Feb. 3-8, 2005.
Nara, et al.; Fourier Transform Infrared Spectroscopic Study on the Ca2+-bound Coordination Structures of Synthetic Peptide Analogues of the Calcium-binding Site III of Troponin C; Biopolymers; vol. 82; issue 4; pp. 339-343; Jul. 2006.
Narayan et al.; Clinical trials in head injury (Author Manuscript). J Neurotrauma 19, 503-57 (May 2002).
Nauta et al.; Silver impregnation of degenerating axons in the central nervous system: a modified technic. Stain Technol 29, 91-3 (Mar. 1954).
Northington et al.; Early Neurodegeneration after Hypoxia-Ischemia in Neonatal Rat Is Necrosis while Delayed Neuronal Death Is Apoptosis. Neurobiol Dis 8, 207-19 (Apr. 2001).
Oda et al.; Magnetic field exposure saves rat cerebellar granule neurons from apoptosis in vitro. Neurosci Lett 365, 83-6 (Jul. 22, 2004).
Ohkubo et al.; Acute effects of static magnetic fields on cutaneous microcirculation in rabbits; In Vivo; vol. 11; pp. 221-226; May-Jun. 1997.
Okano et al.; Biphasic effects of static magnetic fields on cutaneous microcirculation in rabbits; Bioelectromagnetics; vol. 20(3); pp. 161-171; (year of publication is sufficiently earlier than the effective U.S. filing date and any foreign priority date) 1999.
Okie, S.; Traumatic brain injury in the war zone. N Engl J Med 352, 2043-7 (May 19, 2005).
Olbe et al.; The spinach plasma membrane Ca2p pump is a 120-kDa polypeptide regulated by calmodulinbinding to a terminal region; Physiol Plantarum; vol. 103; pp. 35-44; May 1998.
Pantazis et al.; The nitric oxide-cyclic GMP pathway plays an essential role in both promoting cell survival of cerebellar granule cells in culture and protecting the cells against ethanol neurotoxicity. J Neurochem 70, 1826-38 (May 1998).
Papa et al.; Ubiquitin C-terminal hydrolase is a novel biomarker in humans for severe traumatic brain injury. Crit Care Med 38, 138-44 (Jan. 2010).
Pascual et al.; Time course of early metabolic changes following diffuse traumatic brain injury in rats as detected by (1)H NMR spectroscopy. J Neurotrauma 24, 944-59 (Jun. 2007).
Patino et al.; Pulsed electromagnetic fields in experimental cutaneous wound healing in rats. J Burn Care Rehabil 17, 528-31 (Nov./Dec. 1996).
Paylor et al.; Inbred strain differences in prepulse inhibition of the mouse startle response. Psychopharmacology (Berl) 132, 169-80 (Jul. 1997).
Pennington et al.; Pulsed, non-thermal, high-frequency electromagnetic energy (DIAPULSE) in the treatment of grade I and grade II ankle sprains. Mil Med 158, 101-4 (Feb. 1993).
Pfeffer et al.; Disturbed sleep/wake rhythms and neuronal cell loss in lateral hypothalamus and retina of mice with a spontaneous deletion in the ubiquitin carboxyl-terminal hydrolase L1 gene. Neurobiol Aging 43, 393-403, in press, Epub ahead of print (Apr. 2010).
Pilla et al.; EMF signals and ion/ligand binding kinetics:prediction of bioeffective waveform parameters; Bioelectrochemistry and Bioenergetics; vol. 48(1); pp. 27-34; Feb. 1999.
Pilla et al.; Gap junction impedance tissue dielectrics and thermal noise limits for electromagnetic field bioeffects; Bioelectrochemistry and Bioenergetics; vol. 35; pp. 63-69; Nov. 1994.
Pilla, A.; Mechanisms and therapeutic applications of time-varying and static magnetic fields; In: Biological and Medical Aspects of Electromagnetic Fields (eds. Barnes et al.) CRC Press, Boca Raton FL, 351-411 (Oct. 2006).
Pilla; Electrochemical information and energy transfer in vivo; Proc. 7th IECEC;Washington, D.C.; American Chemical Society; pp. 761-764; (year of publication is sufficiently earlier than the effective U.S. filing date and any foreign priority date) 1972.
Pilla; Electrochemical information transfer at living cell membrane; Ann. N.Y.Acad. Sci.; vol. 238; p. 149-170; Oct. 1974.
Pilla; Low-intensity electromagnetic and mechanical modulation of bone growth and repair: are they equivalent?; Journal of Orthopedic Science; vol. 7(3); pp. 420-428; (year of pub. sufficiently earlier than effective US filing date and any foreign priority date) 2002.
Pilla; State of the art in electromagnetic therapeutics: soft tissue applications; Electricity and Magnetism in Biology and Medicine; Bersani (ed.); Kluwer Academic/Plenum Publishers; pp. 871-874; (year of pub. sufficiently earlier than effective US filing date and any foreign priority date) 1999.
Pilla; Weak time-varying and static magnetic fields: from Mechanisms to therapeutic applications; Biological Effects of Electro Magnetic Fields; P. Stavroulakis, ed. Springer Veriag; pp. 34-75; (year of pub. sufficiently earlier than effective US filing date and any foreign priority date) 2003.
Pineros et al.; Calcium channels in higher plant cells: Selectivity, regulation, and pharmacology; J Exp Bot; vol. 48: special issue; pp. 551-577; Mar. 1997.
Pirozzoli et al.; Effects of 50 Hz electromagnetic field exposure on apoptosis and differentiation in a neuroblastoma cell line. Bioelectromagnetics 24, 510-6 (Oct. 2003).
Ramundo-Orlando, et al.; Effect of Low Frequency, Low Amplitude Magnetic Fields on the Permeability of Cationic Liposomes Entrapping Carbonic Anhydrase I. Evidence for Charged Lipid Involvement; Bioelectromagnetics; vol. 21; pp. 491-498; Oct. 2000.
Reale et al.; Modulation of MCP-1 and iNOS by 50-Hz sinusoidal electromagnetic field. Nitric Oxide 15, 50-7 (Aug. 2006).

(56) References Cited

OTHER PUBLICATIONS

Ren et al.; Role of interleukin-1? during pain and inflammation (Author Manuscript). Brain Res Rev 60, 57-64 (Apr. 2009).
Rich et al.; Chronic caloric restriction reduces tissue damage and improves spatial memory in a rat model of traumatic brain injury. J Neurosci Res 88, 2933-9 (Oct. 2010).
Rogers et al.; Behavioral and functional analysis of mouse phenotype: SHIRPA, a proposed protocol for comprehensive phenotype assessment. Mamm Genome 8, 711-3 (Oct. 1997).
Rohde et al.; Effects of pulsed electromagnetic fields on interleukin-1 beta and postoperative pain: a double-blind, placebo-controlled, pilot study in breast reduction patients. Plast Reconstr Surg 125, 1620-9 (1-10) (Jun. 2010).
Ryaby et al.; The role of insulin-like growth factor in magnetic field regulation of bone formation. Bioelectrochem. Bioenergetics; vol. 35(1-2); pp. 87-91; Nov. 1994.
Sagan, L.; Epidemiological and laboratory studies of power frequency electric and magnetic fields; JAMA; vol. 268(5); pp. 625-629; Aug. 5, 1992.
Saljo et al.; Exposure to short-lasting impulse noise causes microglial and astroglial cell activation in the adult rat brain. Pathophysiology 8, 105-111 (Dec. 2001).
Saljo et al.; Low-level blast raises intracranial pressure and impairs cognitive function in rats: prophylaxis with processed cereal feed. J Neurotrauma 27, 383-9 (Feb. 2010).
Salzberg et al.; The effects of non-thermal pulsed electromagnetic energy on wound healing of pressure ulcers in spinal cord-injured patients: a randomized, double-blind study. Ostomy Wound Manage 41, 42-4, 46, 48 passim (Apr. 1995).
Sandyk, R.; Treatment with AC pulsed electromagnetic fields improves olfactory function in Parkinson's disease. Int J Neurosci 97, 225-33 (Apr. 1999).
Sapolsky; Glucocorticoid toxicity in the hippocampus: temporal aspects of neuronal vulnerability. Brain Res 359, 300-5 (Dec. 16, 1985).
Sarimov, et al.; Exposure to ELF Magnetic Field Tuned to Zn Inhibits Growth of Cancer Cells. Bioelectromagnetics; vol. 26; No. 8; pp. 631-638; Dec. 2005.
Sauerland et al.; Risks and benefits of preoperative high dose methylprednisolone in surgical patients: a systematic review. Drug Saf 23, 449-61 (Nov. 2000).
Schmued et al.; Fluoro-Jade: a novel fluorochrome for the sensitive and reliable histochemical localization of neuronal degeneration. Brain Res 751, 37-46 (Mar. 1997).
Seegers et al.; Activation of signal-transduction mechanisms may underlie the therapeutic effects of an applied electric field. Med Hypotheses 57, 224-30 (Aug. 2001).
Shupak et al.; Human exposure to a specific pulsed magnetic field: effects on thermal sensory and pain thresholds. Neurosci Lett 363, 157-62 (Jun. 10, 2004).
Sisken et al.; Prospects on clinical applications of electrical stimulation for nerve regeneration. J Cell Biochem 52, 404-409 (Apr. 1993).
Sisken, et al.; Static magnetic fields and nerve regeneration (presentation abstract); Bioelectromagnetics Society; 21st Ann Meeting, Long Beach, Jun. 20-24, 1999.
Slepko et al.; Progressive activation of adult microglial cells in vitro. Glia 16, 241-46 (Mar. 1996).
Smith, S.; Calcium cyclotron resonance and diatom mobility; Bioelectromagnetics; vol. 8; pp. 215-227; (year of publication is sufficiently earlier than the effective U.S. filing date and any foreign priority date) 1987.
Stahel et al.; The role of the complement system in traumatic brain injury. Brain Res Brain Res Rev 27, 243-56 (Jul. 1998).
Steinberg et al.; Osteonecrosis of the Femoral Head. Results of core decompression and grafting with and without electrical stimulation. Clin Orthop, 199-208 (Dec. 1989).
Teleman et al.; Kinetics of Ca2+ binding to calmodulin and its tryptic fragments studied by 43Ca-NMR. Biochim Biophys Acta 873, 204-13 (Sep. 1986).
Tehranian et al.; Improved recovery and delayed cytokine induction after closed head injury in mice with central overexpression of the secreted isoform of the interleukin-1 receptor antagonist. J Neurotrauma 19, 939-51 (Aug. 2002).
Terpolilli et al.; The novel nitric oxide synthase inhibitor 4-amino-tetrahydro-L-biopterine prevents brain edema formation and intracranial hypertension following traumatic brain injury in mice. J Neurotrauma 26, 1963-75 (Nov. 2009).
Thurman et al.; The epidemiology of sports-related traumatic brain injuries in the United States: recent developments. J Head Trauma Rehabil 13, 1-8 (Apr. 1998).
Trillo et al.; Magnetic fields at resonant conditions for the hydrogen ion affect neurite outgrowth in PC-12 cells: a test of the ion parametric resonance model. Bioelectromagnetics 17, 10-20 (year of publication is sufficiently earlier than the effective U.S. filing date and any foreign priority date) (1996).
Unterberg et al.; Edema and brain trauma. Neuroscience 129(4), 1021-9 (year of publication is sufficiently earlier than the effective U.S. filing date and any foreign priority date) (2004).
Valbona, et al.; Response of pain to static magnetic fields in postpolio patients: A doubleblind pilot study; Arch. Phys. Med. Rehabil.; vol. 78(11); pp. 1200-1203; Nov. 1997.
Vianale et al.; Extremely low frequency electromagnetic field enhances human keratinocyte cell growth and decreases proinflammatory chemokine production. Br J Dermatol 158(6), 1189-96 (Jun. 2008).
Weaver, et al.; The response of living cells to very weak electric fields: The thermal noise limit; Science; vol. 247, No. 4941; pp. 459-462; Jan. 1990.
Weinstein, et al.; Ca2+-Binding and Structural Dynamics in the functions of Calmodulin; Ann. Rev. Physiol; vol. 56; pp. 213-236; Mar. 1994.
Weintraub, M.; Magnetic bio-stimulation in painful diabetic peripheral neuropathy: a novel intervention R a randomized double-placebo crossover study; Am J Pain Manag; vol. 9; pp. 8-17; Jan. 1, 1999.
Weissman et al.; Activation and inactivation of neuronal nitric oxide synthase: characterization of Ca(2+)-dependent [125I]Calmodulin binding. Eur J Pharmacol 435, Jan. 9-18, 2002.
Wenk, G.; The nucleus basalis magnocellularis cholinergic system: one hundred years of progress; Neurobiology of Learning and Memory; 67(2); 85-95 (Mar. 1997).
Williams et al.; Characterization of a new rat model of penetrating ballistic brain injury. J Neurotrauma 22, 313-31 (Feb. 2005).
Yasuda, I.; Part III. Clinical Studies: Mechanical and electrical callus; Annals of the New York Academy of Sciences; vol. 238; pp. 457-465 (Oct. 1974).
Yu et al.; Effects of 60 Hz electric and magnetic fields on maturation of the rat neopallium. Bioelectromagnetics 14, 449-58 (year of publication is sufficiently earlier than the effective U.S. filing date and any foreign priority date) (1993).
Yumoto, et al.; Coordination Structures of Ca2+ and Mg2+ in Akazara Scallop Troponin C in Solution; Eur. J. Biochem; vol. 268(23); pp. 6284-6290; Dec. 2001.
Zaloshnja et al.; Prevalence of long-term disability from traumatic brain injury in the civilian population of the United States, 2005. J Head Trauma Rehabil 23, 394-400 (Nov./Dec. 2008).
Zdeblick; A prospective, randomized study of lumbar fusion: preliminary results; Spine; vol. 18; pp. 983-991; Jun. 15, 1993.
Zhadin, et al.; Frequency and Amplitude Windows in the Combined Action of DC and Low Frequency AC Magnetic Fields on Ion Thermal Motion in a Macromolecule: Theoretical Analysis; Bioelectromagnetics; vol. 26; issue 4; pp. 323-330; May 2005.
Zhadin, et al.; Ion Cyclotron Resonance in Biomolecules; Biomed Sci; vol. 1; pp. 245-250; (year of publication is sufficiently earlier than the effective U.S. filing date and any foreign priority date) 1990.
Zhadin, M.; Combined action of static and alternating magnetic fields on ion motion in a macromolecule; Theoretical aspects; Bioelectromagnetics; vol. 19(5); pp. 279-292; (year of pub. sufficiently earlier than effective US filing date and any foreign priority date) 1998.

(56) References Cited

OTHER PUBLICATIONS

Zhuang et al.; Electrical stimulation induces the level of TGF-B 1 mRNA in osteoblastic cells by amechanism involving calcium/calmodulin pathway; Biochem. Biophys. Res. Comm.; vol. 237;pp. 225-229; Aug. 18, 1997.

Ziebell et al.; Involvement of pro- and anti-inflammatory cytokines and chemokines in the pathophysiology of traumatic brain injury. Neurotherapeutics 7, 22-30 (Jan. 2010).

Zizic et al.; The treatment of osteoarthritis of the knee with pulsed electrical stimulation. J Rheumatol 22, 1757-61 (Sep. 1995).

Klit et al.; Central post-stroke pain: clinical characteristics, pathophysiology, and management; Lancet Neurol.; 8(9); pp. 857-868; Sep. 2009.

Neff; Using pulsed energy therapy for brain injury and concussion; The Headliner; vol. X; Issue 4; pp. 14; Fall 2008 (year of pub. sufficiently earlier than effective US filing date and any foreign priority date).

Strauch et al; Evidence-based use of paulsed electromagentic field therapy in clinical plastic surgery; Aesthetic Surg. J.; 29(2); pp. 135-143; Mar.-Apr. 2009.

World Health Organization; Neurlogical disorders: publiic health challenges; © 2006; 231 pages; retrieved Oct. 26, 2015 from the internet; http://www.who.int/mental_health/neurology/neurological_disorders_report_web.pdf.

Wikipedia; ISM band; 6 pages; retrieved Nov. 30, 2015 from the internet; (https://en.wikipedia.org/w/index.php?title=ISM_band&oldid=690024749).

TWO-PART PULSED ELECTROMAGNETIC FIELD APPLICATOR FOR APPLICATION OF THERAPEUTIC ENERGY

CROSS REFERENCE TO RELATED APPLICATIONS

This patent application claims priority to U.S. Provisional Patent Application No. 61/980,433, filed on Apr. 16, 2014, titled "A TWO-PART PULSED ELECTROMAGNETIC FIELD APPLICATOR FOR APPLICATION OF THERAPEUTIC ENERGY," and U.S. Provisional Patent Application No. 62/086,987, filed on Dec. 3, 2014, titled "A TWO-PART PULSED ELECTROMAGNETIC FIELD APPLICATOR FOR APPLICATION OF THERAPEUTIC ENERGY," each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are pulsed electromagnetic field (PEMF) treatment apparatuses including one or more integrated coils and methods for making and for using PEMF apparatuses for the therapeutic treatment of subjects. More particularly described herein are non-invasive PEMF applicators having two parts: a PEMF generator component, including a power supply and a signal generator, that is adapted to removably couple with a wearable applicator that includes a matched RF power amplifier and impedance matched loop antenna.

BACKGROUND

Weak, non-thermal electromagnetic fields ("EMF") can result in physiologically meaningful in vivo and in vitro bioeffects. See, e.g., U.S. patents and pending applications: U.S. Pat. No. 5,370,680, U.S. Pat. No. 5,584,863, U.S. Pat. No. 5,723,001, U.S. Pat. No. 7,740,574, U.S. Pat. No. 7,744,524, U.S. Pat. No. 7,758,490, U.S. Pat. No. 7,896,797, U.S. Pat. No. 8,343,027, U.S. Pat. No. 8,415,123; U.S. 2010-0210893, U.S. 2010-0222631, U.S. 2013-0274540, U.S. 2014-0046115, U.S. 2014-0046117, U.S. 2011-0207989, U.S. 2012-0116149, and U.S. 2012-0089201, each of which describes PEMF applicator and methods of using them. Each of these publications is herein incorporated by reference in its entirety.

Time-varying electromagnetic fields, comprising EMF, ranging from several Hertz to about 100 GHz, have been found to be clinically beneficial when used as a therapy for reducing pain levels for patients undergoing surgical procedures, promoting healing in patients with chronic wounds or bone fractures, and reducing inflammation or edema in injuries (e.g. sprains). Presently several EMF devices constitute the standard armamentarium of orthopedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

In addition, cellular studies have addressed effects of weak electromagnetic fields on both signal transduction pathways and growth factor synthesis. It has been shown that EMF stimulates secretion of growth factors after a short, trigger-like duration. Ion/ligand binding processes at intracellular buffers attached to the cell membrane are an initial EMF target pathway structure. The clinical relevance to treatments, for example, of bone repair, is up-regulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Pulsed electromagnetic fields ("PEMF") have also been shown to have an effect on transforming growth factor beta ("TGF-β") messenger RNA ("mRNA") in a bone induction model in a rat. Studies have also demonstrated up-regulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue.

Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. U.S. Pat. No. 4,315,503 (1982) to Ryaby, U.S. Pat. No. 7,468,264 (2008) to Brighton and U.S. Pat. No. 5,723,001 (1998) and U.S. Pat. No. 7,744,524 (2010) to Pilla typify the research conducted in this field.

There are currently two types of applicators adapted for applying PEMF. For example, integrated applicators in which the power supply and signal conditioner is integrated into the applicator have been proposed, including those discussed above. Such applicator may be lightweight and wearable, however the operation of the device may be limited by the power supply. Further, although fixedly coupling the signal generator and power amplifier to the antenna delivering the PEMF to the body simplifies the impedance matching between the applicator (antenna) and the power source, the result is somewhat inflexible in operation.

Modular applicators have also been designed, in which the power supply, including the power/signal amplification and waveform/signal generator is separate from the applicator, and may be connected by a cord or wire to one or more applicator. The applicators may be disposable, and typically include only the applicator (e.g., antenna) and connector. This arrangement, while conceptually simple, has various drawbacks. For example, to achieve maximum efficiencies, the impedance of all components of the radio frequency (RF) power pathway must have the same impedance. Thus, the transmission lines and RF connector must have fixed characteristic impedance values. The RF power amplifier and applicator antenna must be impedance matched (e.g., by impedance adjusting circuits) to match the impedance of the cord/transmission line. This arrangement has significant drawbacks for low-power devices. In order to achieve sufficient field strength, the antenna impedance matching circuit must have a high quality factor ("Q-factor") with a very narrow bandwidth. With the normal component variability of high Q-factor components, carrier frequency drift, and tuning variability due to mechanical vibrations, the output field strength may be severely affected, particularly between different applicators connected to the same power supply. Thus, modular PEMF applicators that include separate applicators and power supplies typically require a somewhat complicated (and as a result, large and unwieldy or heavy) power supply portion.

Accordingly, described herein are PEMF applicator systems that may address the need for electromagnetic therapy devices (e.g., PEMF devices) that are simple, lightweight (and wearable) and include a removable/re-attachable signal generator that can couple with one (or more) antenna applicators.

SUMMARY OF THE DISCLOSURE

Described herein are two-part (e.g., modular) PEMF applicator apparatuses and methods of making and using them. In particular, described herein are PEMF applicators that may include: a generator module that includes a power supply (e.g., battery, capacitive power supply, etc.) and signal conditioning (e.g., pulse generator), including timing and control circuitry, but that does not include power amplification or tuning (e.g. impedance matching); and an applicator component that includes power amplification and impedance matching between the amplifier(s) and the delivery antenna(s). The generator and applicator components maybe removably coupleable to each other and the combined generator and applicator can be worn or supported on a subject's body as a lightweight component or part of a delivery component such as a garment (hat, clothing, etc.) or bandage (brace, cast, etc.).

In general, the generator component may include a power supply such as a battery or set of batteries (E.g., AAA alkaline batteries), and may include a processor for preparing the signals (including waveform shaping and timing) to be delivered. The generator component may include a housing that is adapted to mate with an applicator housing that is attached or includes the applicator. Thus, the generator may include a releasable coupling that mates with a coupling on the applicator component to secure the two together. The generator may also be adapted to receive and/or transmit information (e.g., to a microprocessor for control, and/or recording or storing information). The generator may also include one or more indicators for indicating the status of the apparatus (e.g., on/off, delivering PEMF, low power, etc.). The applicator may also include a processor (microprocessor, CPU, etc.) which be used to control operation of the device, including shaping and/or timing of the PEMF waveforms delivered by the applicator.

In general, the applicator unit may include a complimentary coupler for attaching to the generator component. For example, the applicator may include a plug (male, female or hybrid) that couples with the generator. The applicator also includes one or more antenna. In particular, the applicator may include a loop antenna formed of a loop of wire (e.g., having a diameter of 5 inches, 6 inches, 7 inches, 8 inches, 9 inches, 10 inches, 11 inches, 12 inches, etc.). The wire antenna may be flexible/shapeable, and may be positioned over or adjacent to the subject. In some variations the antenna may be integrated into a holder such as a garment or brace. For example, the applicator (including the antenna) may be adapted to fit into a hat or cap to be worn on a subject's head.

The applicator component also typically includes a power amplifier for amplification of signals received by the RF generator of the generator module. The power amplifier may be tuned (automatically or manually) and is integrated into the applicator module/component with the antenna and an impedance match component that matches the impedance of the antenna of the applicator with the power amplifier.

Additional details are provided below including by reference to the figures.

BRIEF DESCRIPTION OF THE DRAWINGS

FIG. 2C is an exploded view of the generator unit shown in FIGS. 6A-6D.

DETAILED DESCRIPTION

Figure 1A:
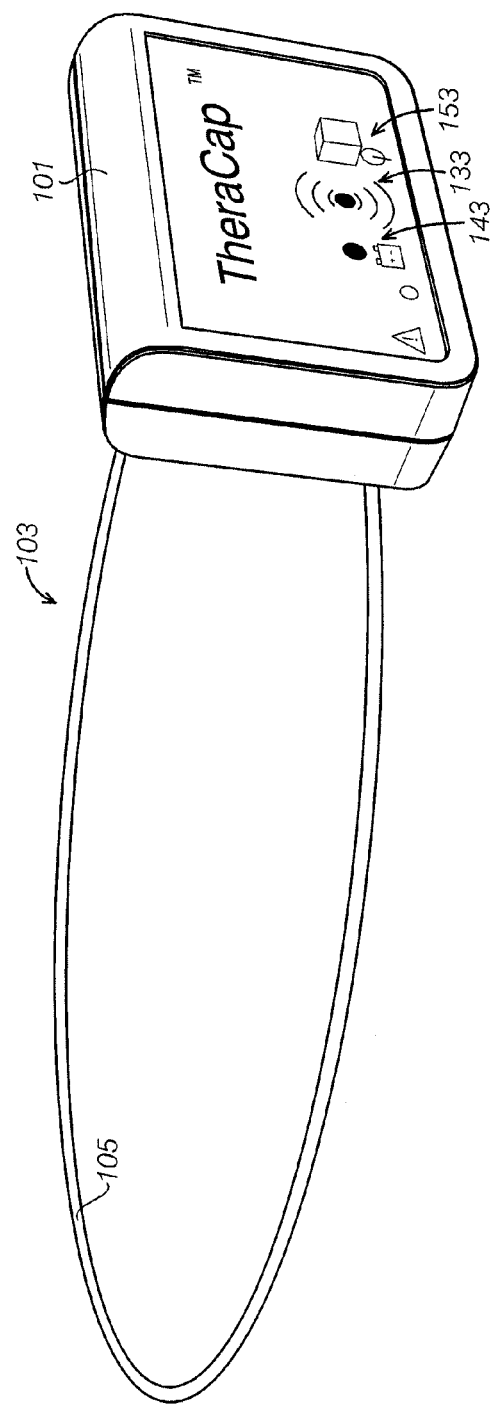
FIG. 1A shows a front perspective view of a two-part therapeutic PEMF apparatus including a generator unit that is coupled to an antenna applicator unit.

Described herein are pulsed electromagnetic field (PEMF) apparatuses and methods of making and using them. In particular, described herein are two-part PEMF apparatuses that include a wearable (e.g., lightweight, small, compact form) generator unit that is adapted to releasably and replaceably mate with an applicator unit. The generator unit, which may also be referred to as a generator module, or generator component, typically includes a power source (e.g., battery, capacitor, etc.), and a controller (e.g., microcontroller and/or microprocessor) and/or waveform generator that generates the RF waveform to be applied as well as controlling the timing. The generator unit may also include a communication module (e.g., wireless module) for communicating with a separate controller/processor for transmitting data (including stimulation history) and/or receiving instructions (including waveform parameters and timing control). The generator unit may also include memory, for storing instructions and/or stimulation history.

In general, the generator unit may be configured so that it does not include any RF power amplification or minimal RF power amplification. Thus, the generator may also be configured so that it does not have impedance matching circuitry. The absence of power amplification and impedance matching circuitry may be an advantage. Surprisingly, the inventors have found that this allows the applicator (e.g., applicator module) to be removable from the generator without suffering radio frequency power losses due to transmission line impedance mismatching.

The applicator unit may also be referred to as an applicator module, antenna unit, antenna module, antenna component and/or applicator component. In general, the applicator unit includes an antenna (such as a wire loop antenna, for inductive or capacitive coupling to the subject's tissues). The antenna may be flexible and may be formed of a loop (e.g., a four inch diameter loop, a five inch diameter loop, a six inch diameter loop, a seven inch diameter loop, an eight inch diameter loop, a nine inch diameter loop, a ten inch diameter loop, an eleven inch diameter loop, a twelve inch diameter loop, etc.) of wire. The wire loop may be bendable and/or configurable, for placement over or against the tissue. The antenna is connected to an impedance matching circuit (including, e.g., tuning circuitry) and connection to an RF power amplifier, which may also include tuning circuitry. Thus, the applicator unit may include impedance matching circuitry for connecting a radio power amplifier to an applicator by intrinsically pairing a high Q-factor impedance matching circuit to the power amplifier and the antenna. The applicator unit can include a plurality of tuning capacitors that can be tuned to provide the desired electric field and frequency. In some embodiments the applicator unit can include a plurality of ports that each allow for access to tuning capacitors in the applicator unit. The tuning capacitors can be tuned by accessing them through the ports. The tuning capacitors can be variable capacitors. A probe can be used to measure the induced voltage of the antenna. The probe can be placed around the middle of the antenna or coil. The tuning capacitors can be adjusted until the induced voltage is at a desired level. In some cases tuning is done such that the induced voltage is greater than about 120 mV.

The antenna can be engaged with a ring-shaped structure to hold the antenna while still allowing movement of the antenna within the ring-shaped structure and movement axially relative to the ring-shaped structure. The ring shaped structures can engage with the hat or be held in place relative to the hat with a clip or other fastener or attachment structure. The ring-shaped structure can non-rigidly engage with the antenna while still allowing movement of the antenna such that the antenna is more comfortable to wear and makes the antenna less likely to deform or break. The ring-shaped structure can be connected to a structure worn by the user to position the antenna relative to a target treatment location on the user. In some cases a plurality of ring-shaped structures can be used to engage the antenna to the structure worn by the user. The ring-shaped structures can be made out of materials such as metal, plastic, polymers, etc. In some cases the ring-shaped structure can be a flexible polymer material, such as a shrink wrap or shrink tubing. In some embodiments the ring-shaped structure can provide some friction to reduce movement between the ring-shaped structure and the antenna while still allowing the antenna to slide relative to the ring-shaped structure.

The generator module is typically adapted to releasably and replaceably mate with the applicator module. Any appropriate connector between the two units may be used, including prongs, plugs, snaps, magnets, Velcro, fasteners, or the like. The connector typically makes an electrical connection between the two so that signals can be transmitted between the generator and the applicator units. Multiple connectors may be used. The connector may be a mechanical connector, an electrical connector, a magnetic connector, or some combination thereof. The connector may also provide physical stability between the two units, preventing physical disruption of the connection. In some variations the apparatus may be configured so that either or both the generator module and the applicator module include a housing that engages with the opposite module.

One variation of a PEMF applicator apparatus is shown in FIG. 1A. In FIG. 1A the apparatus (referred to as "TheraCap" in this example), includes a generator unit 101 that is shown coupled to an applicator unit 103. The applicator unit includes a loop antenna 105. The generator unit may include a power source (e.g., batteries), as well as the circuitry for controlling the operation of the device. The controller (not visible in FIG. 1A) may be a processor (e.g., microprocessor) that is adapted to create and sequence (e.g., time) the RF waveforms to be delivered. The processor or controller may also be adapted to record and/or transmit information about the operation of the device and/or to receive information (control commands) from one or more inputs, including wireless control inputs.

Figure 1B:
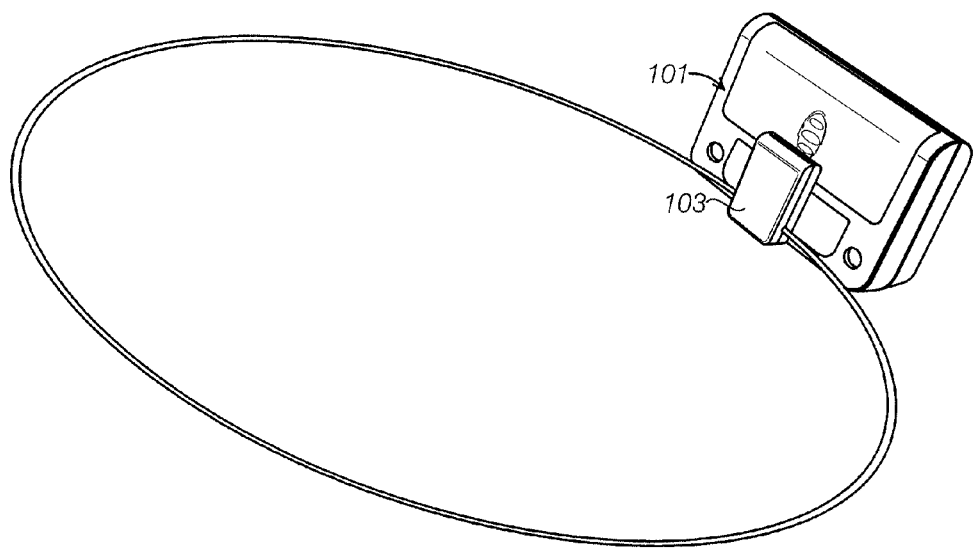
FIG. 1B shows a back perspective view of the apparatus of FIG. 1A.
Figure 1C:
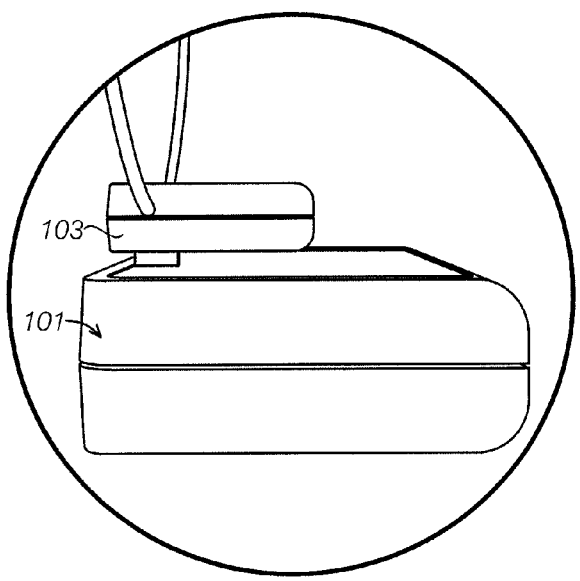
FIG. 1C shows an enlarged view of the coupling between the generator unit and the applicator unit of the PEMF apparatus shown in FIGS. 1A and 1B.

Thus, the generator unit may user controls and outputs. For example, the generator unit may include an output (such as a display screen, LED, indicator light(s), speaker, etc.). The generator unit may also include one or more inputs, including buttons, dials, sliders, switches, etc. The outer portion of the generator may include a housing. Examples of status indicators may include power (power on, power level, charge level) stimulation indicators (indicating when stimulation is being applied), transmission indicators (indicating when data is being received/transmitted by the apparatus), or the like. For example, in FIG. 1A, the face of the generator includes an LED indicating that PEMF is being applied 133, as well as a low battery indicator 143 and a power on/off indicator 153. FIG. 1B shows the back of the apparatus shown in FIG. 1A. The applicator unit 103 is shown connected to the generator unit 101. The applicator unit includes a housing that holds the circuitry including the RF amplifier circuitry, impedance matching circuitry and connects to the antenna. FIG. 1C shows a slightly enlarged view of the coupled applicator unit 103 coupled to the generator unit 101.

Figure 2A:
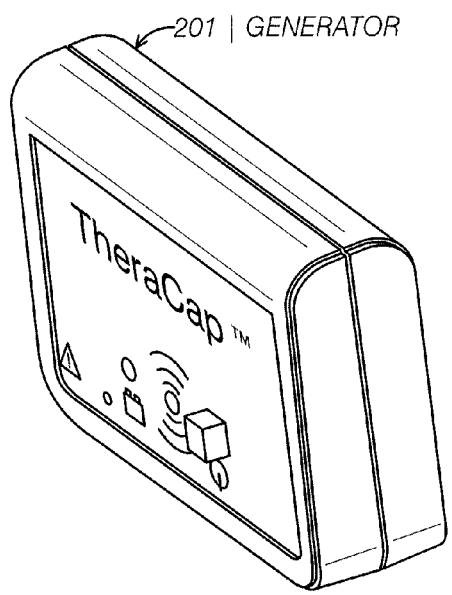
FIG. 2A is a front perspective view of a generator unit of a therapeutic PEMF apparatus.
Figure 2B:
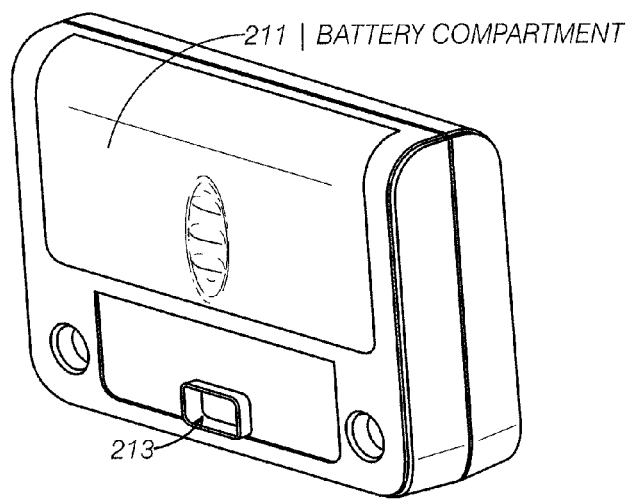
FIG. 2B is a back perspective view of the generator unit of FIG. 2A.

FIGS. 2A and 2B show front and back perspective views, respectively, of one variation of a generator 201. The generator is shown in FIG. 2A to include an outer housing having a front panel including inputs and outputs (e.g., manual inputs and visual outputs). The back of the housing shown in FIG. 2B includes a door that can open to reveal a battery compartment 211. The back housing also includes an opening for a connector 213. The connector in this example is a female plug into which a male connector on the applicator unit (described below) may attach. In some examples additional attachment sites may be included to connect the generator and the applicator.

FIG. 2C shows an exploded view of the generator shown in FIGS. 2A and 2B. In this example, the generator includes a two-part housing (top generator housing 219 and bottom generator housing 217) that may be used to enclose the controller and other generator components. The housing may be fastened together in any appropriate means, including snaps, screws 217, or the like. For example, the housing may enclose the power supply (shown in FIG. 2C as two AAA alkaline batteries 215) behind a removable door (battery flap 221). The controller may be part of the internal circuitry. For example, a printed circuit board (PCB) 221 may be housed within the housing and may include the controller/processor as well as any communications module. As mentioned above, the controller/processor may include the signal generator for generating waveforms of the desired frequency and timing. Examples of the desired waveforms are described in U.S. Pat. No. 5,370,680, U.S. Pat. No. 5,584,863, U.S. Pat. No. 5,723,001, U.S. Pat. No. 7,740,574, U.S. Pat. No. 7,744,524, U.S. Pat. No. 7,758,490, U.S. Pat. No. 7,896,797, U.S. Pat. No. 8,343,027, U.S. Pat. No. 8,415,123; U.S. 2010-0210893, U.S. 2010-0222631, U.S. 2013-0274540, U.S. 2014-0046115, U.S. 2014-0046117, U.S. 2011-0207989, U.S. 2012-0116149, and U.S. 2012-0089201, each of which is again herein incorporated by reference in its entirety.

FIGS. 3A-3D show examples of front, back, bottom and side views, respectively of a housing of a generator module, including exemplary dimensions. For example, in FIG. 3A, the front of the housing may include outputs such as an audio indicator 305, a low battery indicator 307, an activity indicator 309. One or more inputs (e.g., manual inputs) may also be included, such as a power control 310 (e.g., for turning the device on/off). A start/stop control may also be included. The applicator may also include a couple/uncouple control for coupling the generator to the applicator unit. A couple/uncouple control may prepare the units for attaching and detaching, initiating calibration or matching between the devices, and may engage or disengage the coupling elements holding the two units together. In some variations a coupling/uncoupling control may also trigger a self-check or diagnostic testing, or a shutdown/startup sequence. In general the generator unit may detect when it is connected or disconnected from the applicator unit, and may trigger an error code if disconnected (or if the connection degrades), including if disconnecting without using a disconnection procedure (e.g., pushing a coupling/uncoupling control).

Figure 3B:
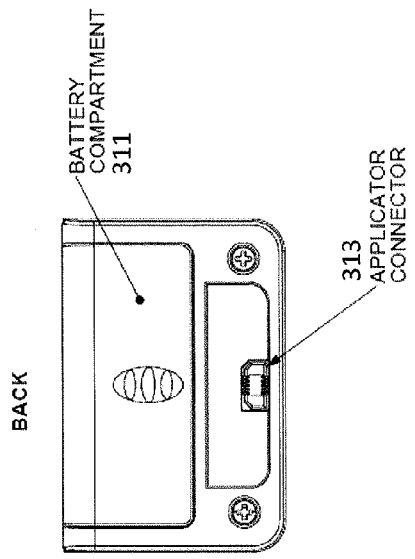
FIG. 3B shows a back view of the generator unit shown in FIG. 3A.
Figure 3D:
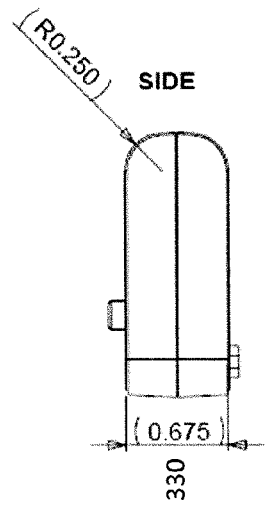
FIGS. 3C and 3D illustrate bottom and side views of the generator unit shown in FIG. 3A.
Figure 3A:
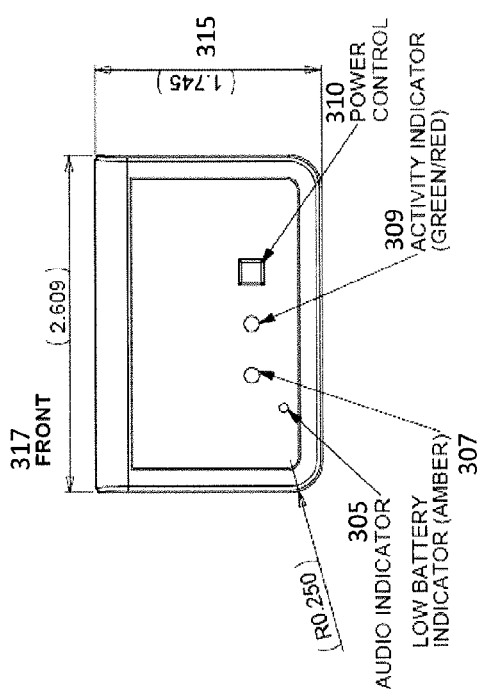
FIG. 3A is an exemplary front view of a generator unit of a two-part therapeutic PEMF apparatus, including exemplary dimensions.
Figure 3C:
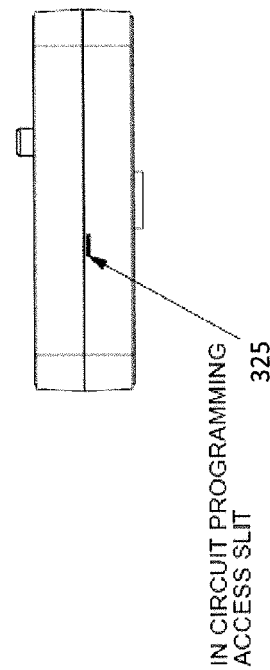

In FIG. 3C, the bottom of the device is shown, and an in-circuit programming access slit 325 is included, allowing access to the controller/processor. This access may allow in circuit programming without the need to dismantle the enclosure or replace hardware (e.g., IC chips). As mentioned above the controller/processor (e.g., CPU) may include flash memory, enabling parameters to be stored for the use and operation of the device. Information on the operation of the device may be stored and/or transmitted, including the stimulation parameters, run times, error codes related to failure or behavior of the apparatus, the number of treatments applied, etc. Control information, including the waveform configurations, timing (e.g., frequency of application, duration of application, burst frequency within an application, etc.) may be stored within the device and modified by modification of the controller.

FIG. 3D shows a side view of the generator, including a proposed thickness 330 (e.g., 0.675 inches). Other dimensions are indicated in FIG. 3A (e.g., height 315 of 1.1745 inches, and width 317 of 2.609 inches). In general, these dimensions are intended as exemplary only. Generally the dimensions may be larger or smaller than those indicated. For example, the overall thickness may be much thinner (e.g., less than 0.5 inches, etc.). The smaller dimensions may allow a lighter, and more readily wearable device. As shown in FIG. 3D, one or more edges of the device may be rounded or radiused. As the device is to be worn, this may be beneficial.

Figure 4A:
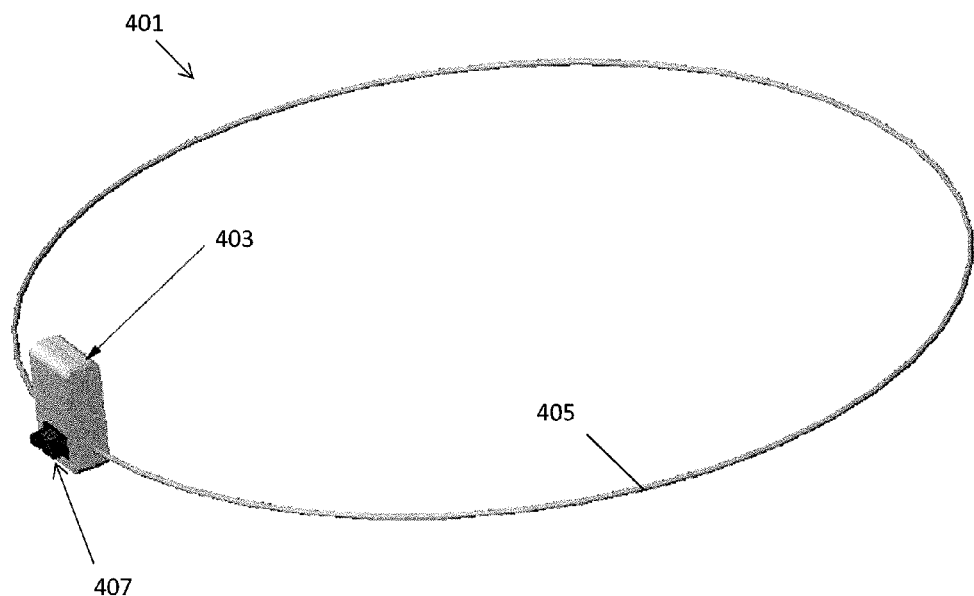
FIG. 4A is a front perspective view of the applicator (or antenna) unit.
Figure 4B:
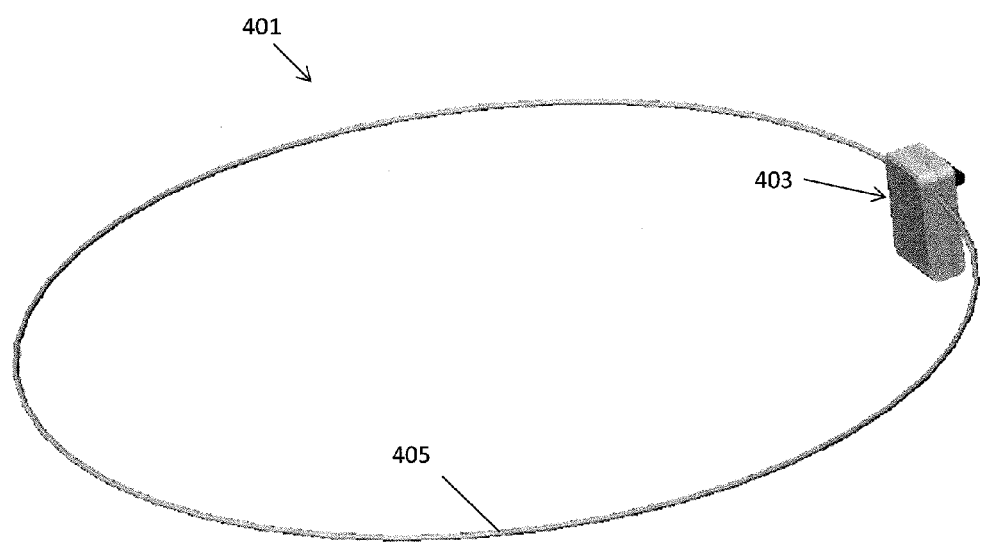
FIG. 4B is a back perspective view of the applicator unit of FIG. 4A.
Figure 4C:
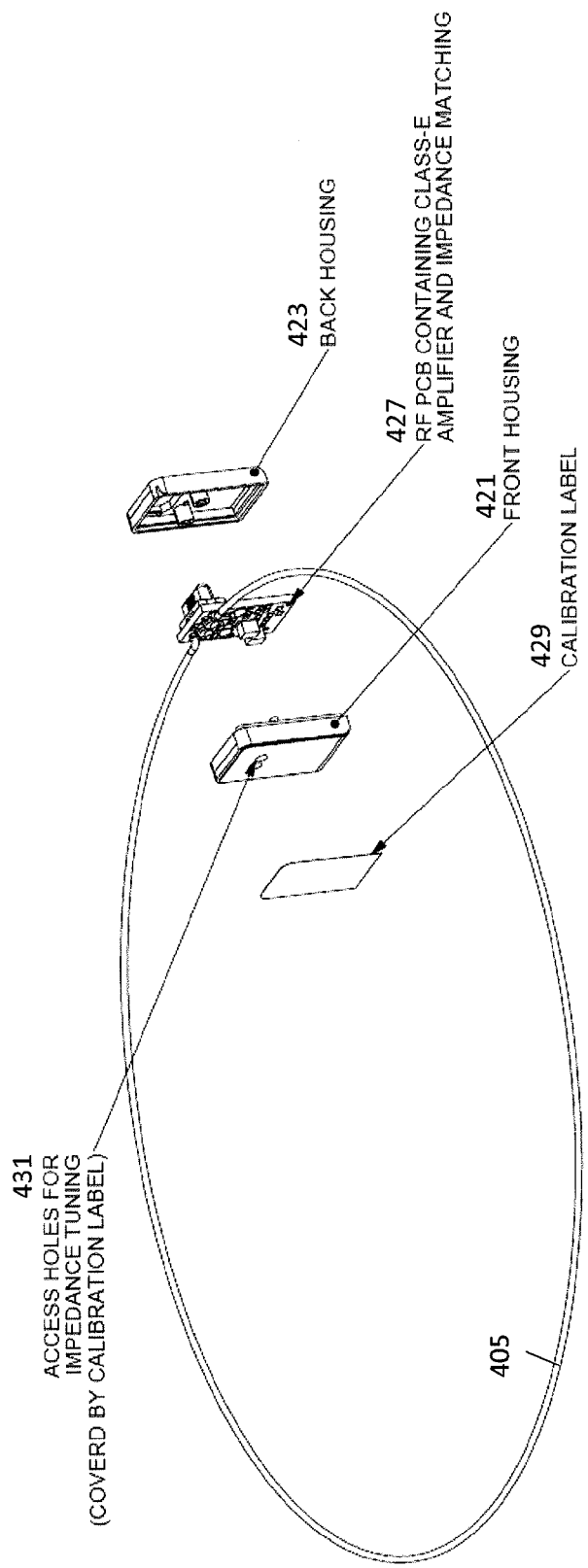
FIG. 4C shows an exploded view of the applicator unit of FIGS. 4A and 4B.

An example of an applicator unit is shown in FIGS. 4A-4C. For example in FIG. 4A, a side perspective view of an applicator module 401 is shown. The applicator unit 401 may include an antenna (in this example, a wire loop antenna 405 is shown. The wire loop antenna shown may be flexible, and bendable, so as to form against the body, or be shaped to permit it to conform to the body. An applicator unit housing 403 is also shown, from which the flexible wire loop antenna 405 extends. One or more coupling elements that are complimentary to connectors or couplers on the generator may be included on the applicator unit. For example in FIG. 4A, and male connector 407 extends from the applicator unit housing 403. The applicator unit may also include one or more sensors (e.g., touch sensors) as mentioned above, which may detect when the unit is being worn on or against a subject. For example, a touch sensor (capacitive touch sensor) on the applicator unit housing 403 may detect when the applicator is being worn against a subject's skin Because the energy may be delivered from the antenna though the skin, and even though clothing or bandages, a sensor may be adapted to sense the presence of the subject though one or more intervening layers.

The connector 407 may be any appropriate connector, and typically electrically couples the generator to the applicator unit. Thus electrical signals may be transmitted to the applicator unit from the generator (e.g., the waveform to be applied). In some variations, as well the applicator unit has a touch sensor, data may be transmitted from the applicator unit to the generator unit. FIG. 4B shows an alternative view of the applicator unit of FIG. 4A, showing the back of the applicator unit housing 40.

FIG. 4C shows an exploded view of the applicator unit housing of FIGS. 4A and 4B. In this example, the applicator unit housing includes a front housing 421 and a back housing 423 than enclose a circuitry (e.g., on printed circuit board, PCB 427) that typically includes RF amplification circuitry (e.g., class E amplified) and impedance matching circuitry and connections to the loop antenna 405. The housing may include one or more openings (e.g. holes 431) for access to and/or controls for tuning the impedance matching. In FIG. 4C a label or cover 429 ("calibration label") may cover these openings. One or more contact sensors (not visible in the example of FIG. 4C) maybe included, e.g., off or on the back housing 423.

The tuning of the device can be changed by adjusting the capacitance of one or more capacitors in the applicator unit. The one or more holes 431 can provide access to the tuning capacitors within the applicator unit. The tuning capacitors can be variable capacitors. In some embodiments there are two variable capacitors with a first variable capacitor connected to a first end of the loop antenna 405 and a second variable capacitor connected to a second end of the loop antenna 405. The variable capacitors can be adjusted such that the loop antenna 405 produces a PEFM signal or waveform with desired characteristics. The use of a plurality of tuning capacitors allows for the operator or user to quickly adjust the capacitance of the device to allow for more control over the treatment conditions. For example, tuning the capacitors allows for the user to adjust the device properties by balancing between the generator unit and applicator unit.

In some embodiments the tuning can be performed by placing a probe on the coil. In some cases the probe is placed on the middle of the coil. The probe can be placed on the desired area of the coil that will be closest to the target treatment area of the user. In one example the coil can be tuned such that the applied field results in an induced voltage on the probe that is greater than about 120 mV. In some embodiments the tuning capacitors allow for individual tuning of the applicator to the proper frequency by adjusting the capacitors.

Figure 5A:
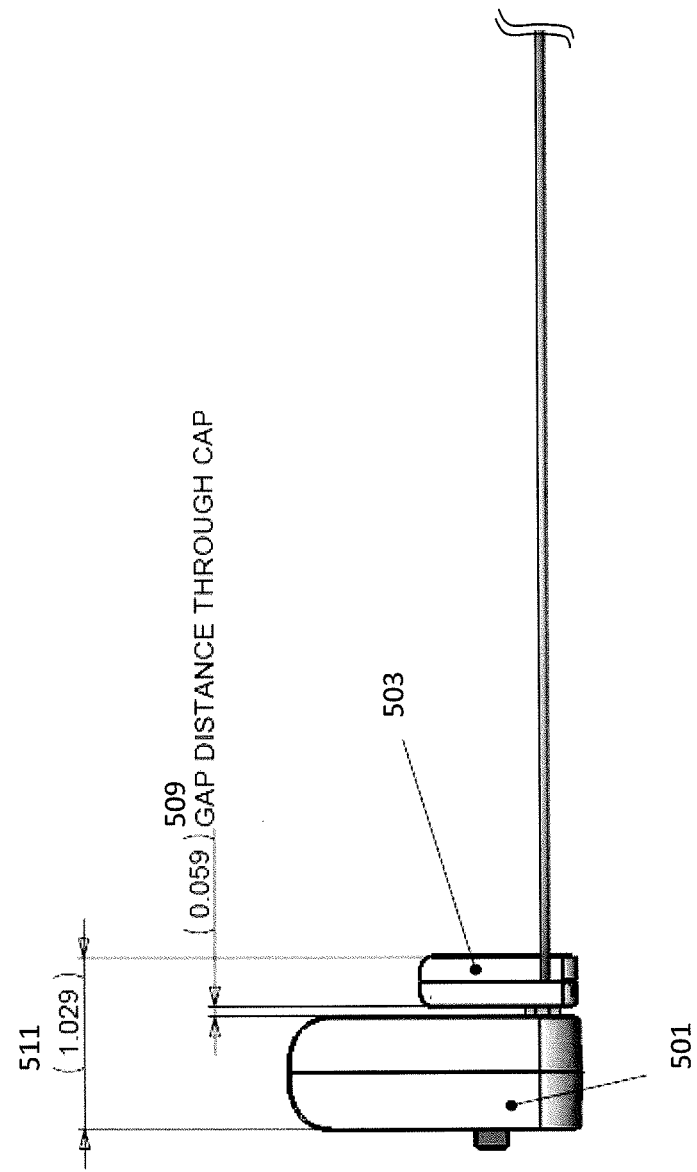
FIG. 5A shows a side view, including exemplary dimensions, of a PEMF apparatus including a generator module and an applicator module. The loop antenna is partially cut off in this figure.
Figure 5B:
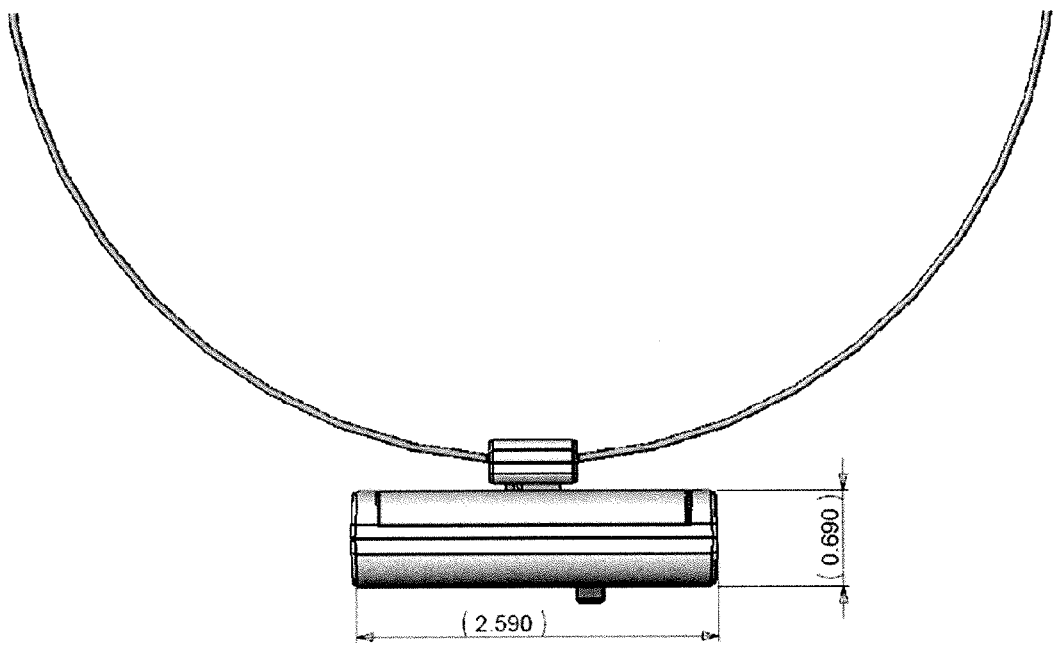
FIG. 5B is a partial top view, including exemplary dimensions, of the PEMF apparatus of FIG. 5A. The loop antenna is partially cut off in this figure.
Figure 5C:
FIG. 5C is a partial front view, including exemplary dimensions, of the PEMF apparatus of FIGS. 5A and 5B. The loop antenna is partially cut off in this figure.
Figure 6:
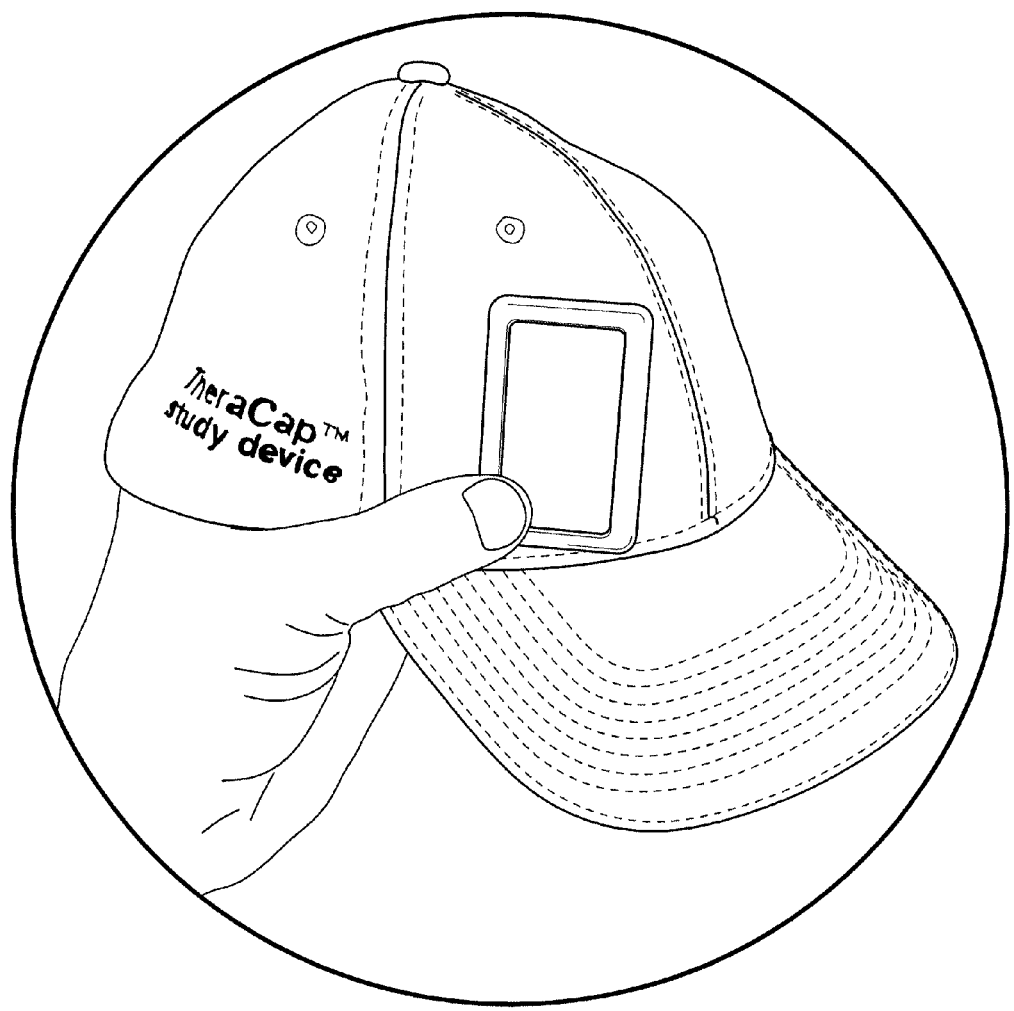
FIG. 6 illustrates one variation of a wearable two-part therapeutic PEMF apparatus configured in a baseball cap, with the applicator integrated into the cap and the generator unit configured to be attached and removed from the cap as necessary.

The generator unit may be combined with applicator unit, as illustrated in FIGS. 5A-5C, to form the apparatus. In FIG. 5A, the generator unit 501 is attached/coupled to the applicator unit 503 though an article of clothing (such as a cap, bandage, garment, etc.). FIG. 6 shows one example of this. In FIG. 5A, the overall thickens of the applicator unit, intervening garment (not shown) and the generator unit 511 is shown as approximately 1.029 inches (assuming a gap/thickness of the intervening garment 509 of 0.059 inches). Thus, the connectors described herein may be adapted to couple the generator unit and the applicator unit in a manner that permits the two to be coupled together through a bandage, garment, cap, helmet, or the like.

FIGS. 5B and 5C show top and front views, respectively, of the partial apparatus shown in FIG. 5A (the applicator antenna is only partially shown in FIGS. 5A-5C). FIGS. 5B and 5C show exemplary dimensions. As mentioned, FIG. 6 shows one example of an applicator attached to a garment (a cap, referred to herein as a "TheraCap"). The cap (hat) includes the applicator on an inner surface (closest to the region worn against the head (not show), e.g., around the brim of the hat. The cap may be adapted for connecting the generator unit with the applicator unit through the cap. For example, a window, opening or the like may be included in the cap where the generator unit and applicator unit may couple to each other. In some variations the cap may include a holder (e.g., frame, pocket, pouch, etc.) to hold the generator.

Figure 7:
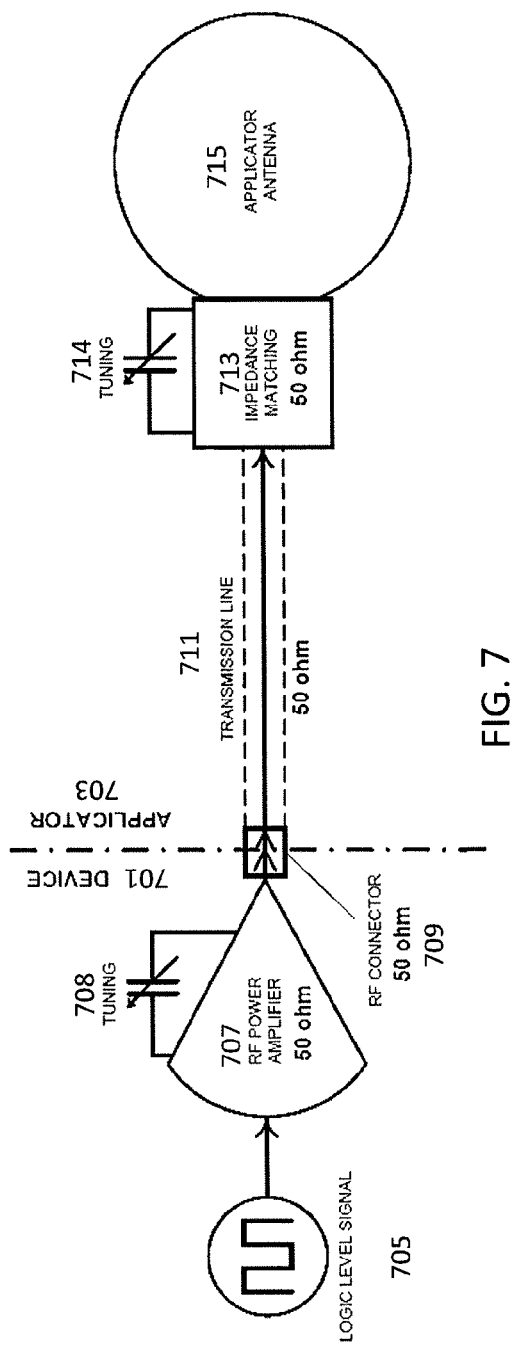
FIG. 7 schematically illustrates a modular PEMF apparatus having an integrated amplification on the generator side (prior art).

In operation, the functions of the PEMF delivery apparatus may be divided between a generator unit and an applicator unit. FIG. 7 shows a schematic of a prior art apparatus in which an amplifier (RF power amplifier) was directly connected/integrated with the signal generator. In FIG. 7, the portion of the device including the signal generator 705 ("device" 701) is directly connected to an RF power amplifier 707 (in this example, the RF power amplifier is a 50 ohm power amplifier that includes tuning circuitry 708 for impedance matching). The device is connected or connectable via an appropriate RF connector 709 (e.g., shown as a 50 ohm connector in FIG. 7), which connects via a transmission line 711 that is also impedance matched (e.g., 50 ohm) to a tunable 714 impedance matching circuit 713 coupled to the applicator antenna 715. In this arrangement, the radio frequency power amplified and applicator antenna impedance matching circuits are separated. To achieve maximum efficiency, the impedance of all components of the RF power pathway must have the same impedance. The transmission line and RF connector have fixed characteristic impedance values (shown in this example as 50 ohms). The RF power amplified and applicator antenna contain impedance-adjustable circuits to match the impedance of the transmission line.

Figure 8:
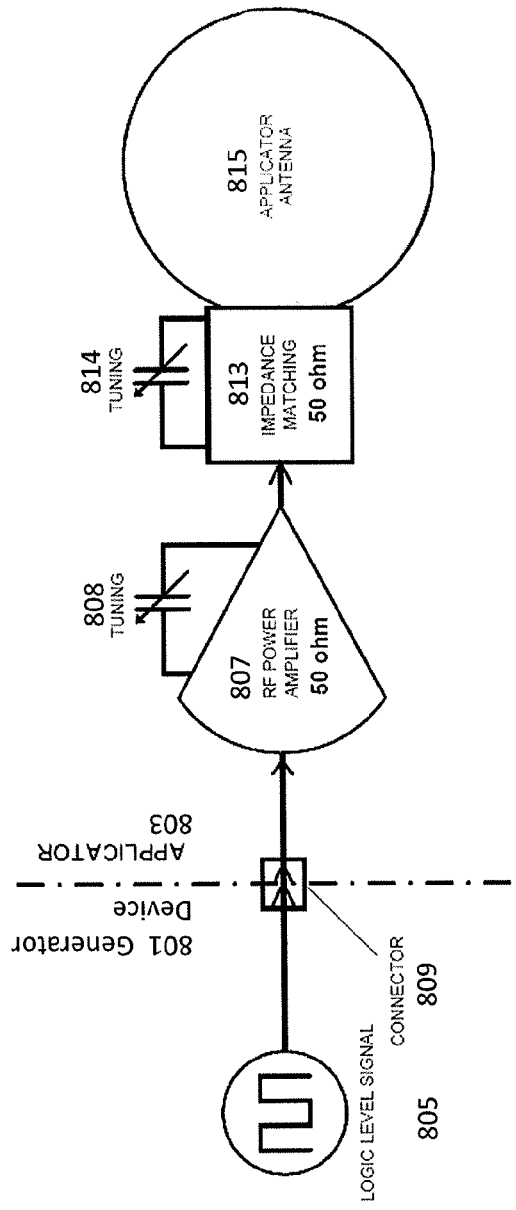
FIG. 8 schematically illustrates a two-part PEMF apparatus in which the RF power amplifier and impedance matching/tuning is present on the applicator unit but not on the generator unit.

FIG. 8 shows a schematic of the apparatuses described herein, in which the separable generator unit 801 includes the signal generator, but not any RF amplification. The RF amplifier is instead included in just the applicator unit 803. As described above, the power amplifier in this example is incorporated into the applicator and intrinsically paired to the high Q-factor impedance matching circuit. This may allow the applicator to be removable without suffering RF power losses due to transmission line impedance miss-matching (e.g., due to poor connection, drift, and noise). In FIG. 8, the processor (controller/processor 805) generates the stimulation waveform having the shape and timing characteristics. The signal transmitted to the amplifier may be unamplified and may be encoded with the amplification information (e.g., including the desired amplification/frequency components) that may be acted on at the applicator by the on-board RF power amplifier 807. The connection 809 between the generator unit 801 and the applicator 803) may be adapted specifically to pass both the signal waveform information (e.g., shape, timing, frequency, etc.) used by the amplifier to apply to the antenna, as well as the power (DC, AC, offset AC, etc.) to drive the applicator unit. As mentioned above, the connector may also pass signals from the applicator to the generator unit (e.g., feedback, sensor information, error codes, etc.). In addition to the RF power amplifier 807, the circuitry in the applicator may include impedance matching/tuning 808/814 circuitry 808, 814, 813 for either or both the RF power amplifier and the applicator antenna 815.

In general, any of the apparatuses described herein may be adapted to operate in a power-saving mode, for example, the applicator and/or generator unit may include a sensor (e.g., capacitive touch sensor) to determine when the unit is in contact with a subject's body. This optional touch sensor may be integrated into the applicator to allow automatic regulation of operation depending on when the apparatus is being worn or not. In general, the generator unit may include a standby mode that consumes little power (e.g., 1 to 19 uA). Standby mode may be entered when the device is not being worn and/or between stimulation periods.

In use, the applicator unit may be attached to a subject's body on, over and/or around the target tissue. Thus, an applicator unit, including the antenna, may be coupled to the patient so that the applicator can be worn. For example, in some variations the target tissue includes the subject's head, for delivery of PEMF to the brain and neural tissue. If the target is the head, for example, the applicator may be worn as part of a cap, hat, helmet, or bandage (see, e.g., FIG. 6). The flexible antenna loop may be placed or present within the brim of the cap, hat, etc. Prior to a desired start of therapy, the apparatus may prepared by connecting a generator unit to the applicator unit. For example a generator unit which is sufficiently charged (e.g., having on-board battery power) may be coupled to the applicator unit worn by the subject. In the example in FIG. 6, a generator unit may be snapped onto the applicator unit worn in the cap. The generator unit may connect by one or more connectors. Connecting may trigger to the generator (controller) that the device is connected and can be used to apply PEMF energy. The apparatus may then run one or more checks to determine and/or confirm the status of the connection. For example, the apparatus may trigger the connection is active and ready for operation. The apparatus may also confirm that the device is ready for operation based on a contact sensor on the device (e.g., indicating that the apparatus is in contact with the subject to be treated. Application of a treatment regime may then begin. The controller in the generator may control the treatment regime (e.g., pulse length, pulse width, pulse duration, repetition rate, etc.). During the process of connecting, activating and treating, one or more indicators may be active or activated. Any appropriate indicators may be used, including visual, audible, thermal and tactile. In particular, a subject may receive tactile feedback that the apparatus is operating when signal/energy (PEMF) is being applied.

Figure 9:
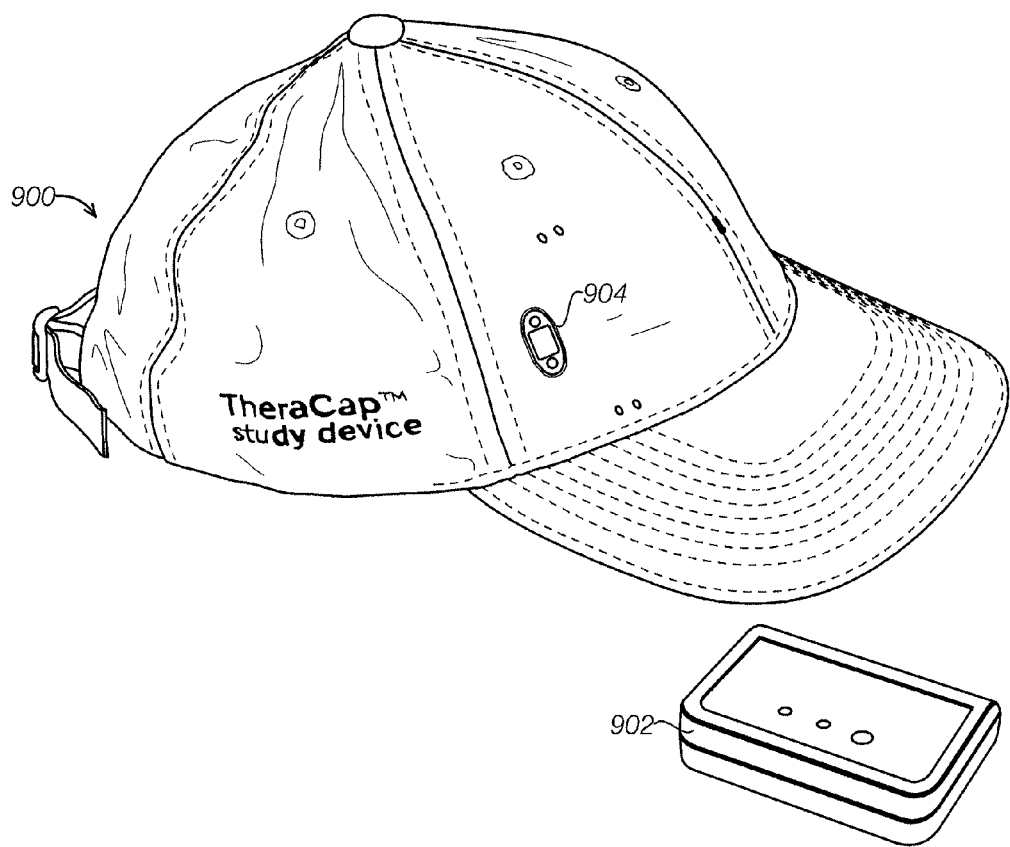
FIG. 9 illustrates an embodiment of a wearable two-part therapeutic PEMF apparatus configured in a baseball cap with the generator not attached to the baseball cap.

FIG. 9 illustrates an embodiment of a wearable two-part therapeutic PEMF apparatus configured in a baseball cap 900 with the generator 902 not attached to the baseball cap 900. The baseball cap 900 includes an opening 904 configured to allow a connector on the generator unit 902 to connect to the applicator unit (not shown). The generator unit 902 includes a magnet that can be used to hold the generator unit to the applicator unit. In some embodiments powerful magnets, such as rare-earth or static magnets are used to hold the generator unit and applicator unit together.

The generator unit with the power supply is held on the outside of the cap. In some cases the generator unit can also be held via a mechanical attachment to the cap, such as using Velcro or other fasteners. The magnetic connection can be used in addition to or instead of a mechanical connection between the generator unit/power supply and the cap. The magnetic connection can securely hold the generator connected to the applicator unit and coil. The magnetic connection allows the generator unit and applicator to be easily and quickly connected.

In the embodiments illustrated in FIG. 9, the loop coil is held in a floating configuration within the inside near the brim of the hat (e.g., edge of the cap). The loop coil is positioned in this location because the target for the effect of the PEMF signal is a region near the midpoint of the frontal lobe. Thus placing the coil in this plane passes the signal through the target treatment location. The coil is held just above the hat band in the embodiments illustrated in FIG. 9. The coil can be positioned anywhere in the cap to deliver the PEMF signal to the target treatment location on the user.

The power supply/generator may be easily swapped out or removed by the user. The generator is held on the right front side of the cap 900 illustrated in FIG. 9. In some embodiments the generator unit may be held anywhere on the cap. In the embodiments illustrated in FIG. 9 the generator location is mostly for aesthetic reasons. In some embodiments the generator unit can be located anywhere along the plane of the coil.

As described herein the generator unit can have a lightweight and small profile. The illustrated generator unit 902 weighs less than about 3 ounces and has a height of less than about 2 inches, a width of less than about 3 inches, and a thickness of less than about 0.5 inches. The generator unit 902 includes a power supply that can include one or more replaceable batteries to power the device. In some embodiments AAA batteries are used. In some embodiments the generator unit can be made smaller and lighter depending on the size of the batteries used for the power supply. The battery can be replaced by removing the generator unit from the hat.

Figure 10:
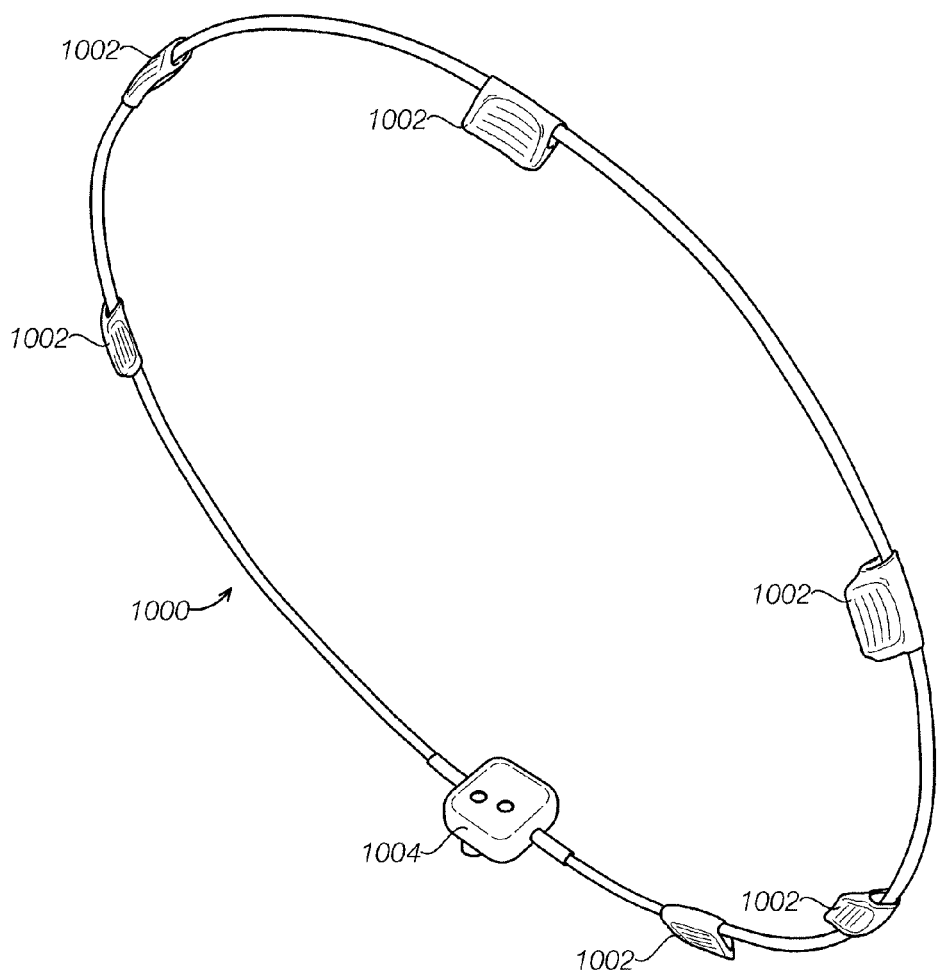
FIG. 10 illustrates a plurality of loop antennas with applicator units in accordance with some embodiments. The loop antennas are illustrated as engaged with ring-shaped structures.

FIG. 10 illustrates a plurality of loop antennas 1000 with applicator units 1004 in accordance with some embodiments. The loop antennas 1000 are illustrated as engaged with a plurality of ring-shaped structures 1002. Each of the loop antennas are illustrated with four ring-shaped structures 1002. The ring-shaped structures 1002 can be attached to the hat via a clip or other attachment mechanism. The ring-shaped structures 1002 include an open channel that holds the loop antenna 1000. The ring-shaped structures 1002 can engage with the hat to hold the loop antenna to the hat in a non-rigid manner. The loop antenna 1000 can slide relative to the ring-shaped structure 1002 axially through the interior volume of the ring-shaped structure and within a plane formed by the interior volume of the ring-shaped structure. The ring-shaped structure 1002 can hold the loop antenna 1000 in approximately the same plane within the hat such that the coil treats the targeted area of the user. The ring-shaped structure 1002 allows the loop antenna 1000 to move within the hat, making the loop antenna 1000 more comfortable to wear and also making it less likely for the loop antenna 1000 to break and/or deform during use. In some embodiments the ring-shaped structure can produce some friction between the loop antenna and the ring-shaped structure. For example the ring shaped structure can be made out of a rubber, shrink wrap material, shrink tubing and/or could have a roughened surface, or other surface that can cause friction against the loop antenna.

Figure 11A:
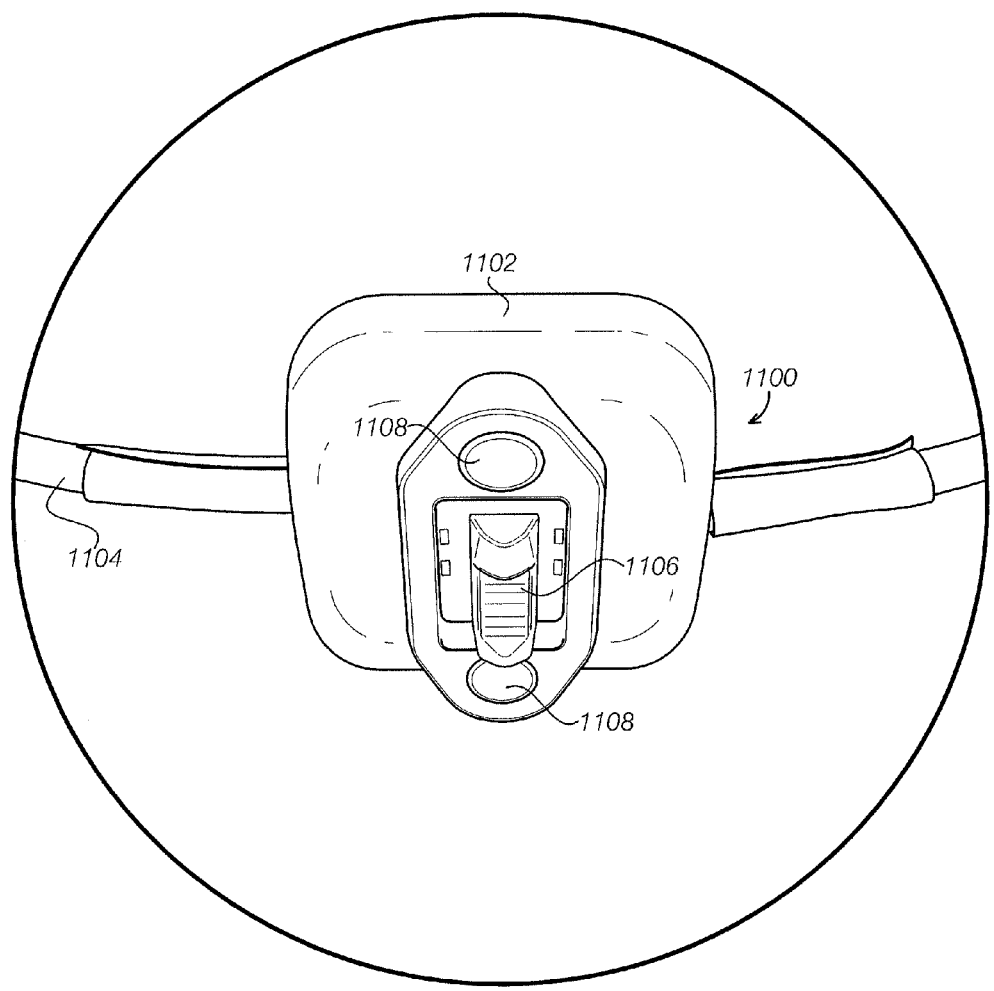
FIGS. 11A-11E illustrates various aspects of a two-part therapeutic PEMF apparatus.
Figure 11B:
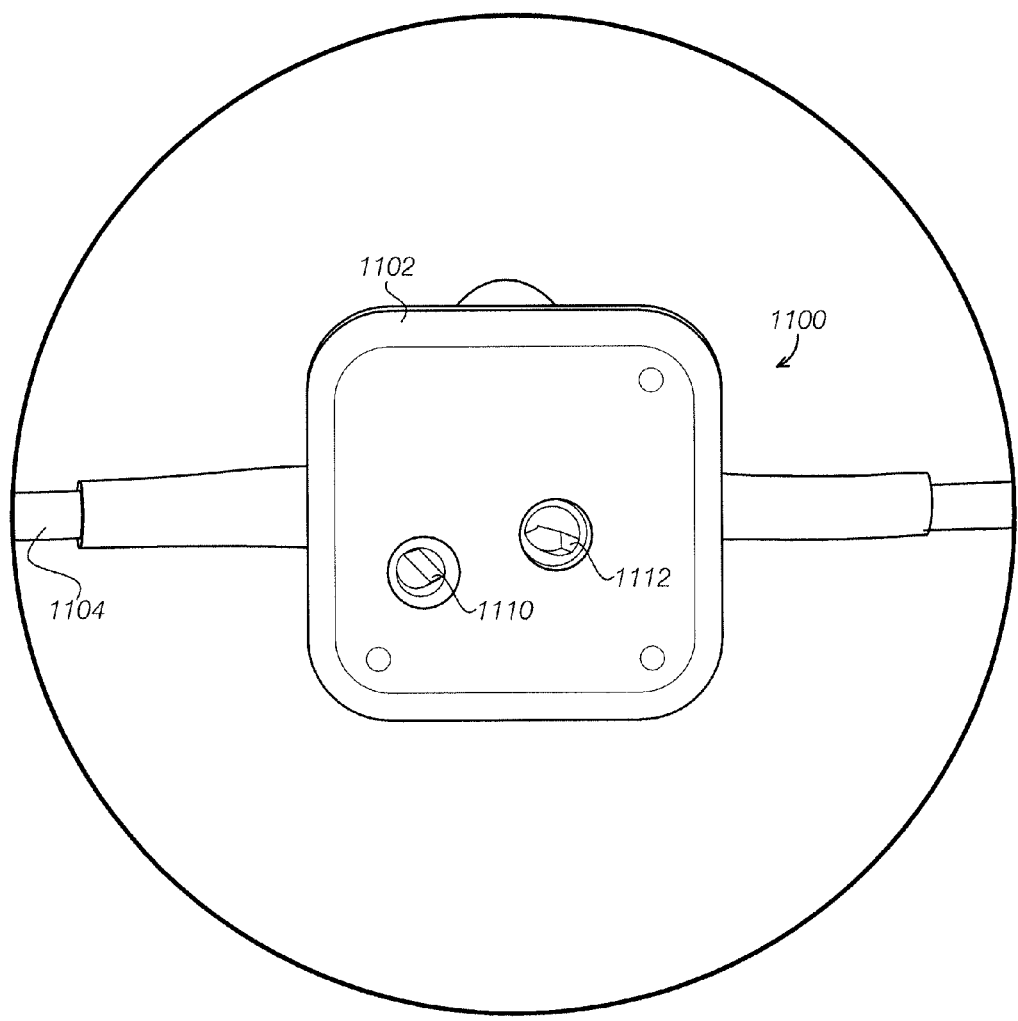
Figure 11C:
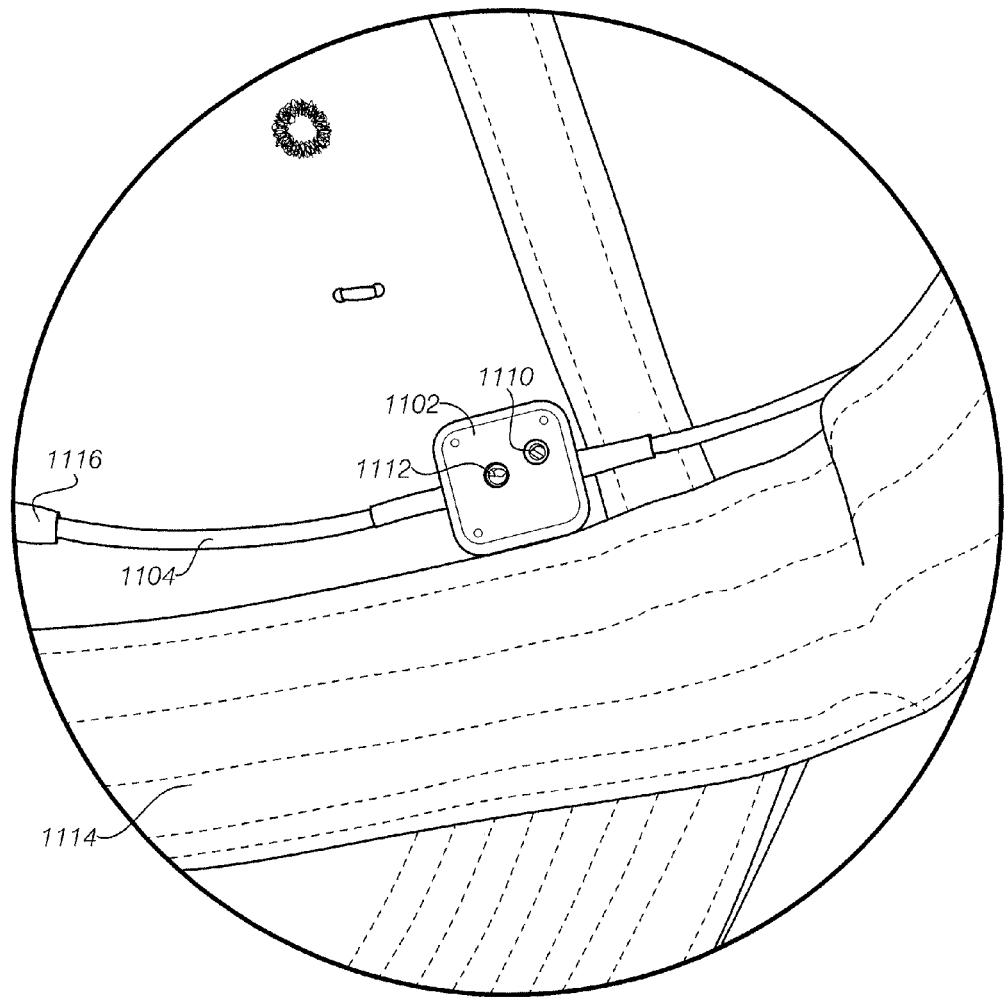
Figure 11D:
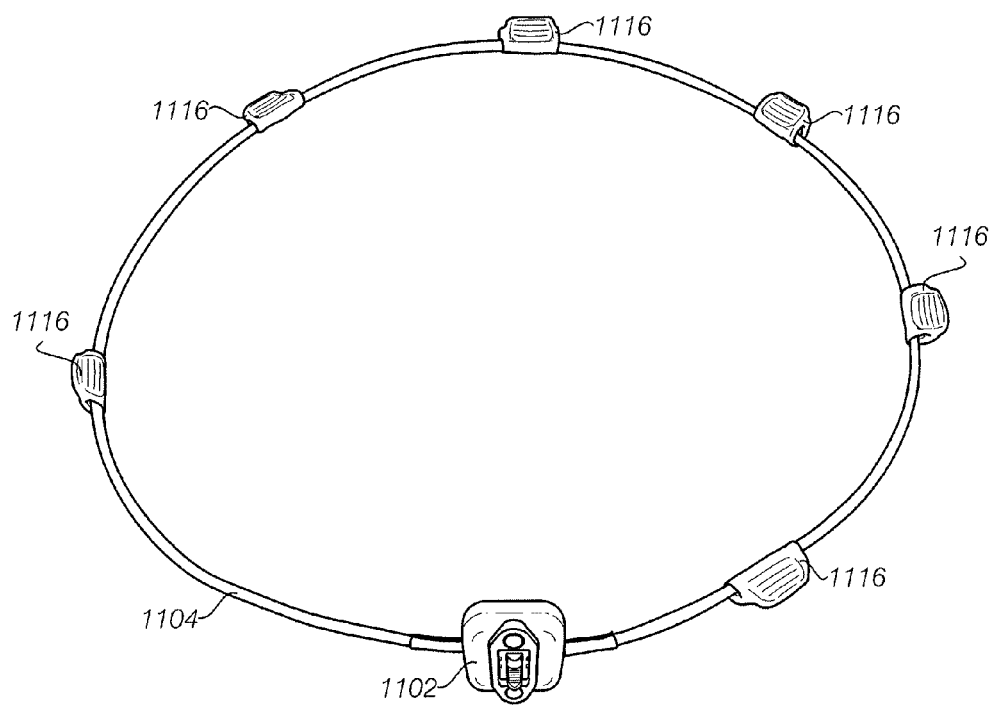
Figure 11E:
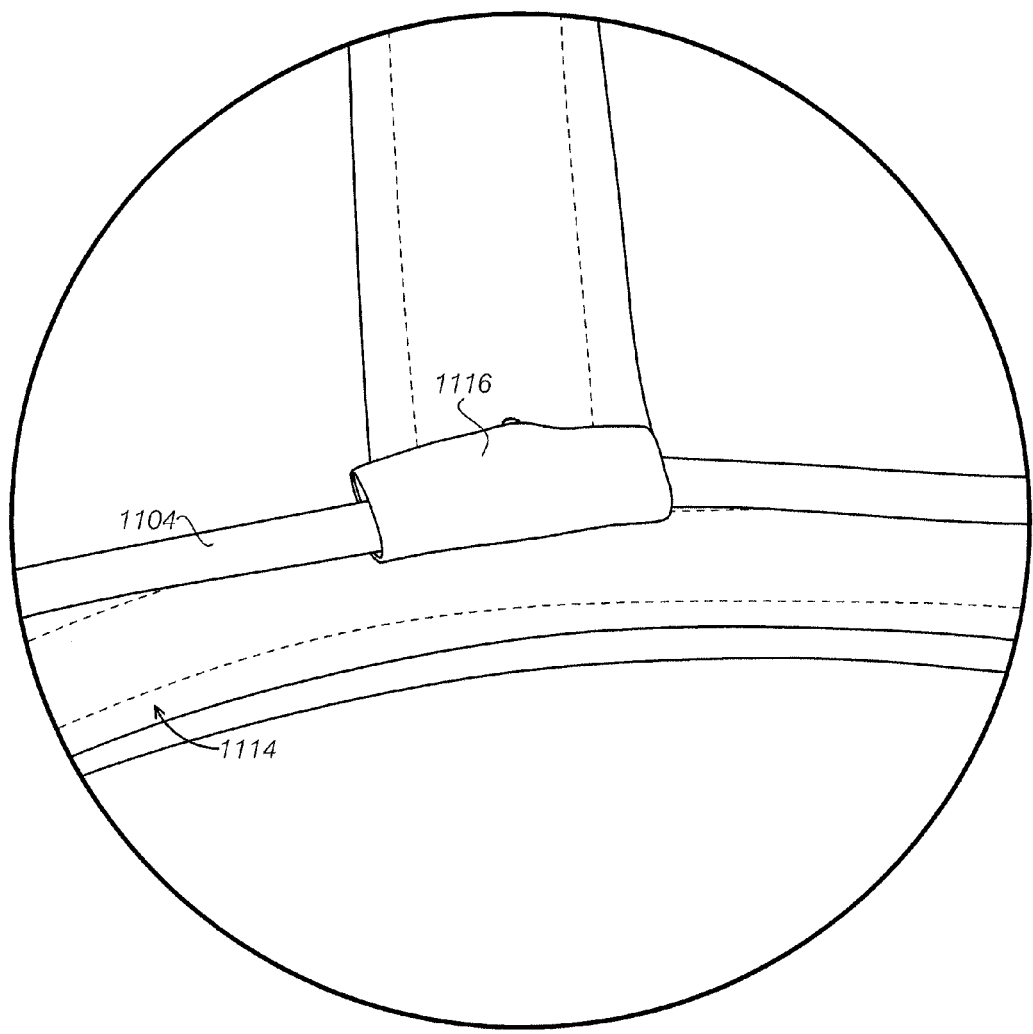

FIGS. 11A-11E illustrate various aspects of a two-part therapeutic PEMF apparatus. FIGS. 11A and 11B illustrate a front view and a back view of a first part 1100 of a two-part PEMF apparatus including an applicator unit 1102 and loop antenna 1104. The back of the applicator unit 1102 includes a connector 1106 and two magnets 1108. The front of the applicator unit 1102 includes a first tuning capacitor 1110 and a second tuning capacitor 1112. The tuning capacitors 1110, 1112 are configured to be tuned by turning a screw head within the housing of the applicator unit 1102. FIG. 11C illustrates the applicator unit 1102 and loop antenna 1104 within a cap 1114. The loop antenna 1104 is engaged with a ring-shaped structure 1116. FIG. 11D illustrates an applicator unit 1102 and loop antenna 1104 engaged with a plurality of ring-shaped structures 1116. FIG. 11E illustrates the loop antenna 1104 secured to the cap 1114 by securing the ring-shaped structure 1116 to the cap 1114. The ring-shaped structure 1116 can be clipped or fastened to the cap 1114 to non-rigidly secure the loop antenna 1104 within the cap 1114. The loop antenna 1104 can slide through the interior volume of the ring-shaped structures 1116.

Figure 12A:
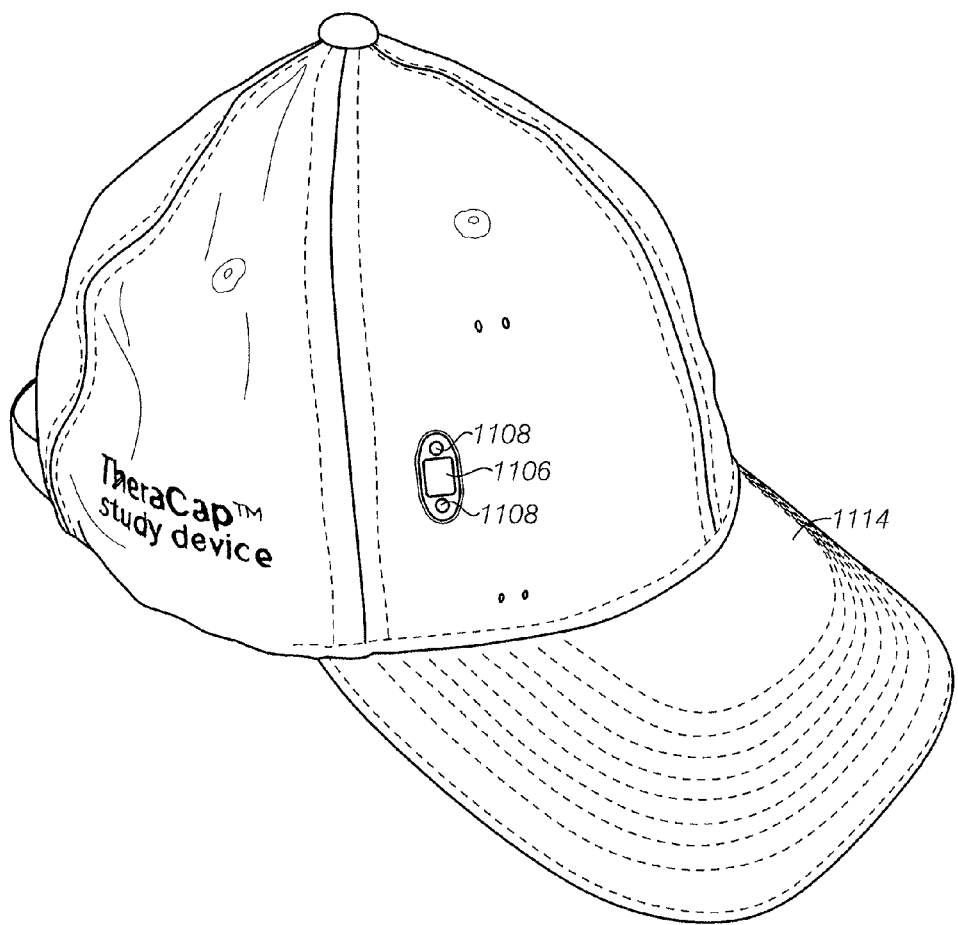
FIGS. 12A-12C illustrate various aspects of a two-part therapeutic PEMF apparatus.
Figure 12B:
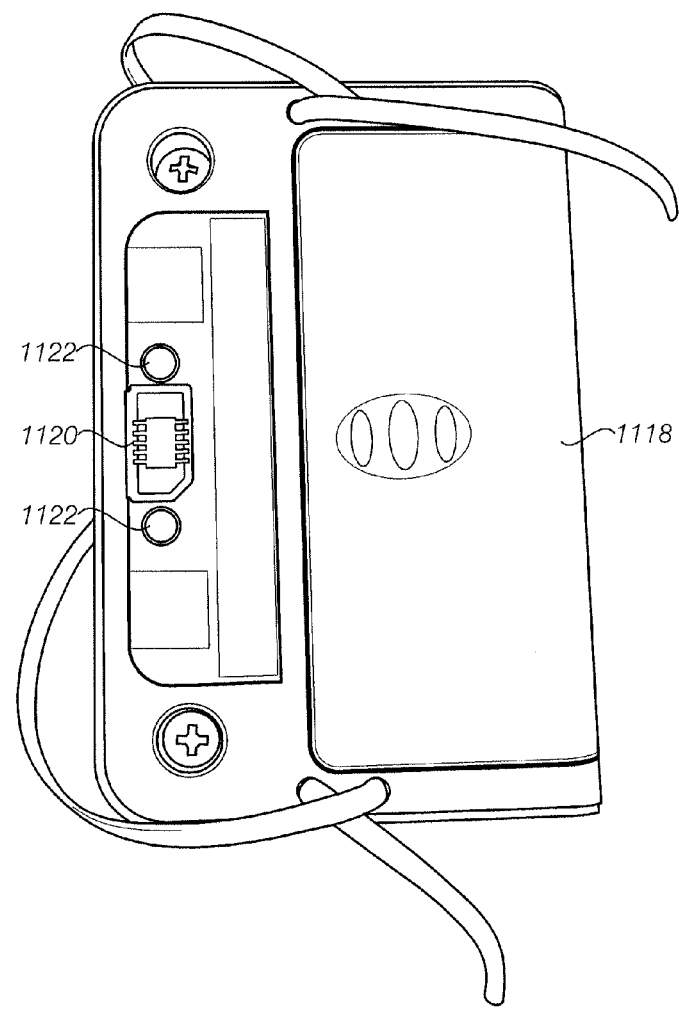
Figure 12C:
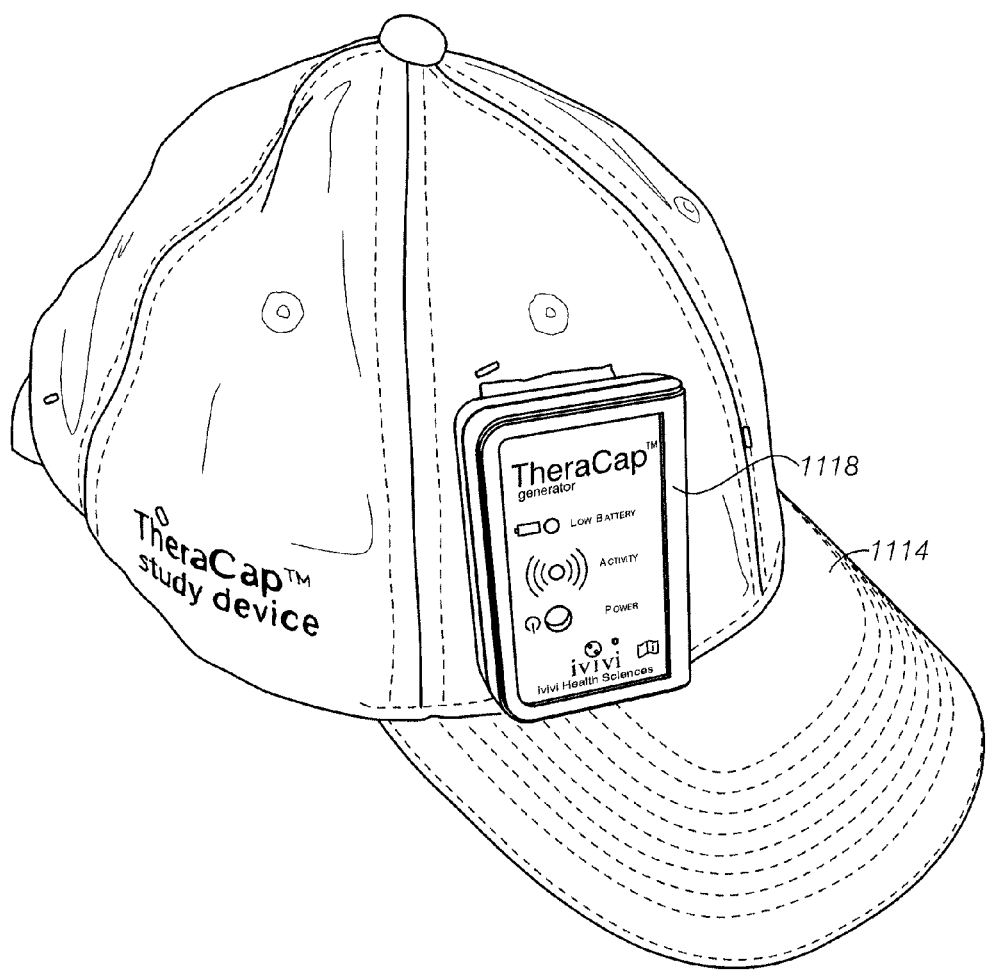

FIGS. 12A-12C illustrate various aspects of a two-part therapeutic PEMF apparatus that can be used with the embodiments illustrated in FIGS. 11A-11E. FIG. 12A illustrates the cap engaged with the applicator unit 1102 such that the connector 1106 and two magnets 1108 protrude through an opening in the cap 1114. FIG. 12B illustrates a generator unit 1118 with a connector 1120 and magnets 1122. The illustrated connector 1120 has a female receptacle that is configured to complementarily engage with the connector 1106 on the applicator unit 1102. The magnets 1122 of the generator unit 1118 are configured to engage with the magnets 1108 of the applicator unit. FIG. 12C illustrates the cap 1118 with the generator unit 1118 engaged with the applicator unit.

Although many of the variations and examples described above are specific to hat or wearable devices, any of these apparatuses may be non-wearable. For example, in some variations the apparatuses are integrated into furniture (e.g., bedding, chairs, etc.) or sleeping devices (e.g., pillows, bedding, mattresses, cushions, etc.), and particularly those configured so that the user places his or her head on the device.

For example, in some variations, the apparatus is configured as a pillow or mattress (e.g., bedding). In FIG. 13A, for example, the apparatus is configured as a travel pillow 1301 that includes an applicator 1304 loop that is incorporated near an outer portion (though internal to the pillow and/or pillow cover). FIG. 13A shows a travel pillow that is engaged with the applicator loop 1304 such that an applicator unit 1302 (similar to the applicator units described above, including one or more connectors, e.g., magnets), that is present on an outer surface of the pillow. The applicator loop 1304 is positioned on a region of the pillow where the user will position her or his head when wearing the pillow, as shown in FIG. 13A.

Any of these apparatuses may also be two-part therapeutic PEMF apparatuses. For example, in FIGS. 13A to 13B, the pillows are configured as two-part PEMF apparatuses and configured so that a first part of a two-part PEMF apparatus including an applicator unit 1302 and loop antenna 1304 is integrated into the pillow. As mentioned, the applicator unit 1302 includes a connector 1306 which may include one or more (e.g., two) magnets. As discussed above, the applicator unit 1302 may also include a first tuning capacitor and a second tuning capacitor (not shown) configured to be tuned by turning a screw head within the housing of the applicator unit 1302.

Any of these pillows may also be marked to indicate "top" or "bottom" or specifically indicate where the applicator is, so that the user can position their head close to the loop. As mentioned, the applicator may be held within the pillow near an outer surface, or in or between a cover (e.g., pillow case) over a cushion of the pillow. In FIG. 13A, the applicator unit 1302 is shown on an upper surface of the pillow, away from the region where the user's head will rest; in general the applicator unit may be located anywhere on (or in some variations, in) the pillow, so that the generator unit 1318 may be connected unobtrusively, but may be easily swapped out. For example, the applicator unit may be located in a pocket that may also hold the generator unit; this pocket may be on an outer surface (not shown) on an inner surface, away from where the head will rest (e.g., on the back portion of the pillow), for comfort. In this example, the pillow or cushion shown is a travel-type pillow configured with a curved/U-shape so that it can fit around a user's neck. In general, the pillow may have any appropriate shape, including traditional rectangular/square shapes, as illustrated in FIGS. 13B (back) and 13C (front).

Figure 13B:
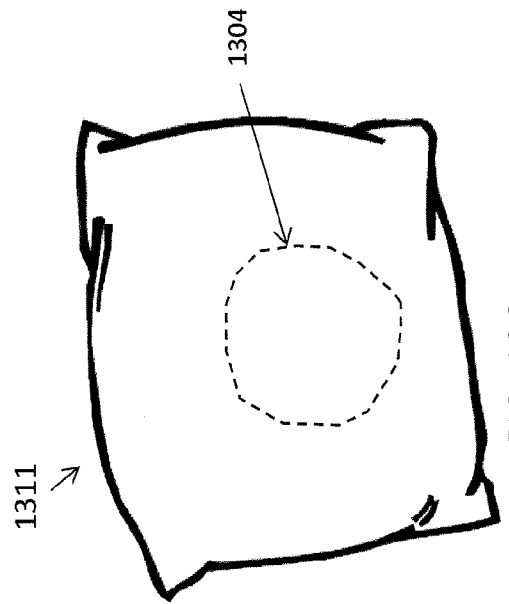
FIGS. 13A-13C illustrate another variation of a two-part therapeutic PEMF apparatus, configured as a pillow such as a travel-type pillow (FIG. 13A) or standard bed pillow (FIGS. 13B-13C).

For example, in FIG. 13B, the back of a pillow 1311 is shown, with the connector 1306 of the applicator unit 1302 located in one corner. In this example, the first part of the two-part apparatus (including the applicator coil) may be integrated into the pillow or into a pillow holder/case in which the pillow fits. A generator unit 1318 that is adapted to connect to the connector of the applicator unit (e.g., by one or more fasteners such as snaps, magnets, etc.) is also shown in FIG. 13B. The connector region of the shown in this example includes a female receptacle that is configured to complementarily engage with the connector 1106 on the applicator unit 1102. The magnets 1122 of the generator unit 1118 are configured to engage with the magnets 1108 of the applicator unit. FIG. 12C illustrates the cap 1118 with the generator unit 1118 engaged with the applicator unit.

Figure 13C:
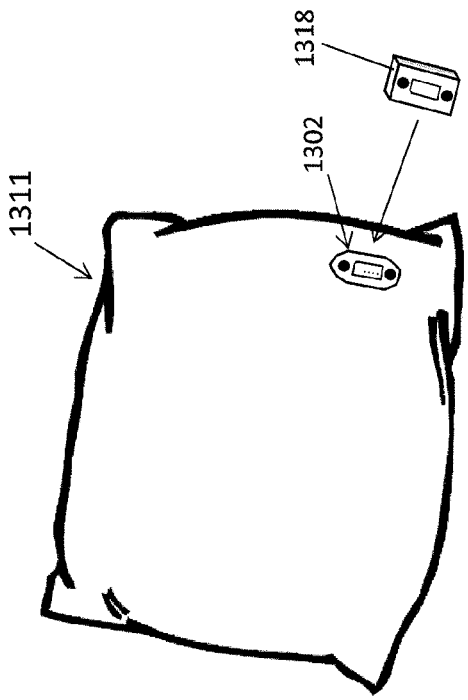
Figure 13A:
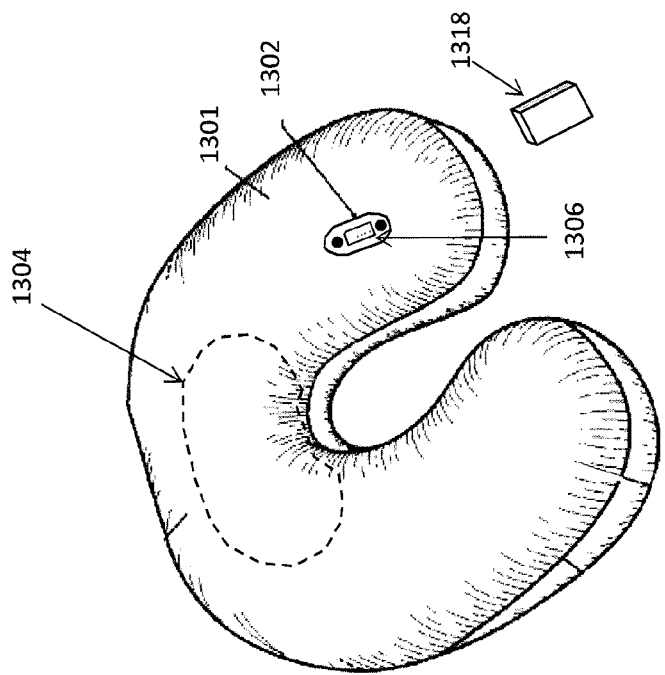

FIG. 13C shows a front view (or top view) of the pillow apparatus of FIG. 13B; the applicator loop 1304 is shown in the dashed lines, as it may be located (and connected to the applicator unit by one or more wires, not shown) within the pillow or pillow covering, or between the pillow and pillow covering, as mentioned above.

In use, any of the two part-devices described herein may be configured so that a first part that is attached to the hat, garment, furniture, pillow, etc., and the second part may be removably attached to the first part to provide power and/or signals to the applicator of the first part. The same second part may be used interchangeably with multiple first parts.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the teems "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all subranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A modular apparatus for applying pulsed electromagnetic field (PEMF) energy to a subject, the apparatus comprising:
   a generator unit including a signal generator configured to generate a PEMF waveform and a first connector;
   an applicator unit including
      a second connector adapted to mate with the first connector,
      a radio frequency (RF) power amplifier adapted to receive waveform information from the generator unit though the second connector and generate PEMF signals therefrom,
      a loop antenna connected to the RF power amplifier and adapted to deliver the PEMF signals to the subject wearing the applicator unit,
      impedance matching circuitry configured to match the impedance between the RF power amplifier and the loop antenna;
   a generator housing enclosing the signal generator; and
   an applicator housing enclosing the RF power amplifier,
   wherein the generator unit is configured to releasably connect to the applicator unit to drive transmission of PEMF signals from the applicator unit based on the PEMF waveforms, further wherein the generator housing and the applicator housing are adapted to engage with each other to releasably connect the generator unit to the applicator unit.

2. The apparatus of claim 1, wherein the generator unit comprises a power source.

3. The apparatus of claim 1, wherein the signal generator comprises a controller including the signal generator.

4. The apparatus of claim 1, further comprising a memory within the generator unit adapted to store information about one or more of applied stimulation, operational status, or error codes.

5. The apparatus of claim 1, wherein the generator unit does not include a separate RF power amplifier.

6. The apparatus of claim 1, further comprising a couple/uncouple control configured to engage or disengage the generator unit from the applicator unit.

7. The apparatus of claim 1, further comprising a wireless communications unit in the generator unit.

8. The apparatus of claim 1, the impedance matching circuitry comprising one or more variable capacitors.

9. A modular apparatus for applying pulsed electromagnetic field (PEMF) energy to a subject, the apparatus comprising:
   a generator unit including a signal generator configured to generate a PEMF waveform and a first connector; and
   an applicator unit including
      a second connector adapted to mate with the first connector,
      a radio frequency (RF) power amplifier adapted to receive waveform information from the generator unit though the second connector and generate PEMF signals therefrom,
      a loop antenna connected to the RF power amplifier and adapted to deliver the PEMF signals to the subject wearing the applicator unit,
      impedance matching circuitry configured to match the impedance between the RF power amplifier and the loop antenna;
   wherein the generator unit is configured to releasably connect to the applicator unit to drive transmission of PEMF signals from the applicator unit based on the PEMF waveforms,
   further wherein the first connector comprises a first magnetic structure on the generator unit and the second connector comprises a second magnetic structure on the applicator unit configured to complementarily engage with the first magnetic structure.

10. A modular apparatus for applying pulsed electromagnetic field (PEMF) energy to a subject, the apparatus comprising:
   a self-contained, lightweight generator unit including a signal generator configured to generate a PEMF waveform and a first connector, wherein the generator unit does not include a separate radio frequency (RF) power amplifier; and an applicator unit, wherein the generator unit is adapted to releasably connect with the applicator unit when the applicator unit is worn by the subject, the applicator unit including:
a second connector adapted to mate with the first connector,
a radio frequency (RF) power amplifier adapted to receive waveform information from the generator unit though the second connector and to generate PEMF signals therefrom,
a loop antenna connected to the RF power amplifier and adapted to deliver the PEMF signals to the subject wearing the applicator unit,
impedance matching circuitry configured to match the impedance between the RF power amplifier and the loop antenna;
wherein the generator unit is configured to power the applicator unit to drive transmission of PEMF signals from the applicator unit based on the PEMF waveforms,
further comprising a generator housing enclosing the signal generator and an applicator housing enclosing the RF power amplifier, wherein the generator housing and the applicator housing are adapted to engage with each other to releasably connect the generator unit to the applicator unit.

11. The apparatus of claim 10, wherein the generator unit comprises a power source.

12. The apparatus of claim 10, wherein the signal generator comprises a controller including the signal generator.

13. The apparatus of claim 10, further comprising a memory within the generator unit adapted to store information about one or more of applied stimulation, operational status, or error codes.

14. The apparatus of claim 10, further comprising a couple/uncouple control configured to engage or disengage the generator unit from the applicator unit.

15. The apparatus of claim 10, further comprising a wireless communications unit in the generator unit.

16. The apparatus of claim 10, wherein the impedance matching circuitry comprises one or more variable capacitors.

17. A modular apparatus for applying pulsed electromagnetic field (PEMF) energy to a subject, the apparatus comprising:
a self-contained, lightweight generator unit including a signal generator configured to generate a PEMF waveform and a first connector, wherein the generator unit does not include a separate radio frequency (RF) power amplifier; and
an applicator unit, wherein the generator unit is adapted to releasably connect with the applicator unit when the applicator unit is worn by the subject, the applicator unit including:
a second connector adapted to mate with the first connector,
a radio frequency (RF) power amplifier adapted to receive waveform information from the generator unit though the second connector and to generate PEMF signals therefrom,
a loop antenna connected to the RF power amplifier and adapted to deliver the PEMF signals to the subject wearing the applicator unit,
impedance matching circuitry configured to match the impedance between the RF power amplifier and the loop antenna;
wherein the generator unit is configured to power the applicator unit to drive transmission of PEMF signals from the applicator unit based on the PEMF waveforms,
wherein the first connector comprises a first magnetic structure on the generator unit and wherein the second connector comprises a second magnetic structure on the applicator unit configured to complementarily engage with the first magnetic structure.

\* \* \* \* \*